(12) United States Patent
Du et al.

(10) Patent No.: US 11,465,958 B2
(45) Date of Patent: *Oct. 11, 2022

(54) PROCESS FOR FRIEDEL-CRAFTS REACTION, AND CATALYST THEREFORE

(71) Applicant: Fujian Yongjing Technology Co., Ltd., Fujian (CN)

(72) Inventors: Hongjun Du, Fujian (CN); Wenting Wu, Fujian (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/517,546

(22) Filed: Jul. 20, 2019

(65) Prior Publication Data

US 2020/0262775 A1 Aug. 20, 2020

(30) Foreign Application Priority Data

Feb. 15, 2019 (DE) .......................... 102019103840.5

(51) Int. Cl.
*C07C 45/46* (2006.01)
*B01J 27/08* (2006.01)
(Continued)

(52) U.S. Cl.
CPC .............. *C07C 45/46* (2013.01); *B01J 27/08* (2013.01); *C07C 17/269* (2013.01);
(Continued)

(58) Field of Classification Search
None
See application file for complete search history.

(56) References Cited

U.S. PATENT DOCUMENTS

| 4,453,009 A | 6/1984 | Yamaguchi et al. |
| 4,814,508 A | 3/1989 | Gors et al. |

(Continued)

FOREIGN PATENT DOCUMENTS

| CN | 1935758 A | * | 3/2007 |
| CN | 104744392 | | 7/2015 |

(Continued)

OTHER PUBLICATIONS

Olah, G. A. et al. "Hydrogen Fluoride-Antimony(V) Fluoride" eEros, Apr. 15, 2001, pp. 1-8 (Year: 2001).*

(Continued)

*Primary Examiner* — Medhanit W Bahta

(57) ABSTRACT

The invention relates to a new process for the manufacture of fluoroaryl compounds and derivatives thereof, in particular of fluorobenzenes and derivatives thereof, and especially wherein said manufacture relates to an environmentally friendly production of the said compounds. Thus, the present invention overcomes the disadvantages of the prior art processes, and in a surprisingly simple and beneficial manner, and as compared to the prior art processes, in particular, the invention provides a more efficient and energy saving processes, and also provides a more environmentally friendly process, for the manufacture of nuclear fluorinated aromatics, and preferably of nuclear fluorinated fluorobenzenes. Accordingly, in one aspect of the invention, an industrially beneficial process for preparing fluorobenzenes from halobenzene precursors using HF to form hydrogen halide is provided by the present invention. A beneficial and surprisingly simple use of chlorobenzene as an industrially interesting starting material in the manufacture of fluorobenzene is provided.

11 Claims, 2 Drawing Sheets

(51) Int. Cl.
*C07C 17/269* (2006.01)
*C07C 201/12* (2006.01)
C07C 22/08 (2006.01)
C07C 49/813 (2006.01)
C07C 205/12 (2006.01)

(52) U.S. Cl.
CPC ............ *C07C 201/12* (2013.01); *C07C 22/08* (2013.01); *C07C 49/813* (2013.01); *C07C 205/12* (2013.01)

(56) References Cited

U.S. PATENT DOCUMENTS

| | | | |
|---|---|---|---|
| 5,300,693 | A | 4/1994 | Gilb et al. |
| 5,633,405 | A | 5/1997 | Thompson et al. |
| 6,600,074 | B2 | 7/2003 | Onishiet et al. |
| 2001/0041814 | A1 | 11/2001 | Tohnishi et al. |
| 2004/0127757 | A1 | 7/2004 | Iikubo et al. |
| 2017/0217865 | A1* | 8/2017 | Gribkov ................ C07C 201/08 |

FOREIGN PATENT DOCUMENTS

| | | | |
|---|---|---|---|
| CN | 104844412 | A * | 8/2015 |
| CN | 106008182 | | 10/2016 |
| CN | 106045828 | | 10/2016 |
| CN | 107573500 | | 1/2018 |
| DE | 3531837 | | 3/1987 |
| EP | 0582455 | | 2/1994 |
| EP | 0919542 | | 6/1999 |
| EP | 1380568 | | 1/2004 |
| EP | 1626047 | | 2/2006 |
| EP | 1637271 | | 5/2011 |
| JP | 2014237738 | | 12/2014 |
| WO | WO03053580 | | 7/2003 |
| WO | WO2018055384 | | 3/2018 |

OTHER PUBLICATIONS

Yoneda, N. et al. "Electrophilic Substitution of Benzenes With Strong Electron-Withdrawing Groups in Super Acid Media, Friedel-Crafts Alkylation of Acetophenone" Chemistry Letters, pp. 1003-1006, 1979 (Year: 1979).*

Repinskaya, I. B. et al. Zhurnal Organicheskoi Khimii, vol. 21, Issue: 4, pp. 836-845 (1985) (Year: 1985).*

Allgemein ("High-performance ceramic microreactors in a single piece" Apr. 27, 2007) (Year: 2007).*

CN1935758A, English translation, Mar. 2007, pp. 1-2 (Year: 2007).*

Patent No. CN104844412A, Machine translation, Aug. 2015, pp. 1-11 (Year: 2015).*

Dai, G. et al. "Synthesis of ciprofloxacin" Zhongguo Yiyao Gongye Zazhi, vol. 23, Issue: 4, pp. 153-154, Journal, 1992; Abstract and Reaction scheme only, pp. 1-2 (Year: 1992).*

Konovalov, A. I. et al. "Ruthenium-catalyzed nucleophilic fluorination of halobenzenes" Chem. Commun., 2015, 51, 13527 (Year: 2015).*

Dai, G. et al. "Synthesis of ciprofloxacin" Zhongguo Yiyao Gongye Zazhi, vol. 23, issue 4, pp. 153-154 (Year: 1992).*

* cited by examiner

PROCESS FOR FRIEDEL-CRAFTS REACTION, AND CATALYST THEREFORE

BACKGROUND OF THE INVENTION

Field of the Disclosure

The invention relates to a new process for the manufacture or synthesis, respectively, of acylated or alkylated aryl compounds, for example, acylated or alkylated benzenes, by the so-called Friedel-Crafts reaction, and a new catalyst therefore.

Description of Related Art

Friedel-Crafts reactions, for example, are used in the industrial manufacture of PAEKs (polyaryletherketones), and especially of PEEK (polyetheretherketones).

For example, PEEK is made out of condensation of hydroquinone with 4,4'-difluorobenzophenone, and this benzophenone is made out of fluorobenzene as key raw material like described in Victrex WO2018/055384 and also patents in Faming Zhuanli Shenqing (2018), CN 107573500. The 4,4'-difluorobenzophenone is either made out of 4,4'-difluorodiphenylmethane by oxidation (ChemCatChem (2018), 10(5), 1096-1106) or alternatively out of Friedel-Crafts alkylation reaction of fluorobenzene with $CCl_4$ (HuagongJinzhan (2015), 34(4), 1104-1108) or Friedel-Crafts acylation of fluorobenzene with 4-fluorobenzoylchloride like mentioned in Raychem's U.S. Pat. No. 4,814,508. The most common synthesis of difluorodiphenylmethane as of today is the synthesis out of 4,4'-methylenebis[benzenamine] by Balz-Schiemann reaction involving dirty $NaNO_2/HBF_4$ chemistry like described by Faming ZhuanliShenging (2016), in CN 106008182, and by other authors. The synthesis of difluorodiphenylmethane out of fluorobenzene and formaldehyde is described in early days already in Bulletin de la SocieteChimique de France; (1951); p. 318, 323 or out of 4-fluorobenzylchloride like in Journal of the Chemical Society, Chemical Communications (1989)(18), 1353-4.

Another Friedel-Crafts acylation based synthesis of 4,4'-difluorobenzophenone is out of fluorobenzene, or alternatively starting from 4-fluorophenylboronic acid like described in Chemical Communications (Cambridge, United Kingdom) (2017), 53(93), 12584-12587 and a 4-fluorobenzoic acid derivative or 4-fluorotrichlorotoluene derivative like described in Faming ZhuanliShenging (2016), CN 106045828. All these processes involve at least in one of the steps a Balz-Schiemann reaction combined with a Friedel-Crafts reaction. Both reaction types are quite old technologies which might have to be replaced by newer environmentally friendly chemistries and reaction technologies. The synthesis of 4,4'-difluorobenzophenone out of 4,4'-dichlorobenzophenone by "dirty" Halex reaction is described in Mitsui's patent U.S. Pat. No. 4,453,009. The said Halex chemistry in general is considered "dirty" due to incomplete conversion, and isolation of product is challenging and often produces large amounts toxic waste water. The "dirty" KCl obtained as coupling product is often used for landfill.

In general a Friedel-Crafts reaction of benzoylchloride with chlorobenzene in state of the art reactors (Lewis acid catalyzed in ionic liquids) is known as described in Chemistry Letters (2008), 37(8), 844-845 and Journal of the Chinese Chemical Society (Taipei) (2000), 47(6), 1243-1246, also the Friedel-Craft in microreactors with $\alpha$-$Fe_2O_3$ and $CaCO_3$ nanoparticles is already described like in Chemical Engineering Journal (Amsterdam, Netherlands) (2018) 331, 443-449. The Friedel-Crafts reaction of chlorobenzene with chlorobenzoylchloride with AlCl3 as Lewis acid is described with 96% yield in HuagongXinxingCailiao (2012), 40(2), and 87-90% and in Journal of Fluorine Chemistry (2005), 126(8), 1191-1195 by using rare earth (III) perfluorooctane sulfonates in fluorous solvents with 86% yield.

The reaction of chlorobenzene with terephtaloylchloride is known from KhimicheskayaTekhnologiya (Moscow, Russian Federation) (2001)(5), 3-5, at temperatures around 260° C. without Friedel-Crafts Catalyst and with 86% yield and also in Qingdao KejiDaxueXuebao, ZiranKexueban (2007), 28(1), 39-42 using AlCl3 and Jpn. KokaiTokkyoKoho (2014), JP 2014237738 using FeCl3 as Lewis acid.

Friedel-Crafts reaction of chlorobenzylchloride and chlorobenzene is described in Journal of Organic Chemistry (1989), 54(5), 1201-3, and AngewandteChemie, International Edition (2011), 50(46), 10913-10916.

For example, Friedel-Crafts reaction may be useful regarding the manufacture of benzophenone. The preferred IUPAC name of benzophenone is diphenylmethanone; other names include benzophenone, phenyl ketone, diphenyl ketone, benzoylbenzene, benzoylphenyl, benzoylphenyl, diphenylmethanone; the CAS Number is 119-61-9.

In the prior art benzophenone is produced by the copper-catalyzed oxidation of diphenylmethane with air. A laboratory route involves the reaction of benzene with carbon tetrachloride followed by hydrolysis of the resulting diphenyldichloromethane. It can also be prepared by Friedel-Crafts acylation of benzene with benzoyl chloride in the presence of a Lewis acid (e.g., aluminium chloride) catalyst. Another route of synthesis is through a palladium(II)/oxometalate catalyst. This converts an alcohol to a ketone with two groups on each side. Another, less well-known reaction to produce benzophenone is the pyrolysis of anhydrous calcium benzoate.

Regarding properties, diphenyldichloromethane is an organic compound with the formula $(C_6H_5)_2CCl_2$. It is a colorless solid that is used as a precursor to other organic compounds.

Diphenyldichloromethaneis prepared, in the prior art, from carbon tetrachloride and anhydrous aluminium chloride as catalyst in a double Friedel-Crafts alkylation of benzene. Alternatively, benzophenone is treated with phosphorus pentachloride:

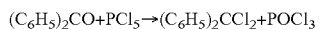

$(C_6H_5)_2CO+PCl_5 \rightarrow (C_6H_5)_2CCl_2+POCl_3$

Diphenyldichloromethaneundergoes hydrolysis to benzophenone:

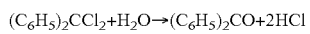

$(C_6H_5)_2CCl_2+H_2O \rightarrow (C_6H_5)_2CO+2HCl$

Diphenyldichloromethaneis used in the synthesis of tetraphenylethylene, diphenylmethane imine hydrochloride and benzoic anhydride.

Regarding diphenylmethane, diphenylmethane is an organic compound with the formula $(C_6H_5)_2CH_2$. The compound consists of methane wherein two hydrogen atoms are replaced by two phenyl groups. Diphenylmethane forms a common skeleton in organic chemistry; the diphenylmethyl group is also known as benzhydryl. It is prepared by the Friedel-Crafts alkylation of benzyl chloride with benzene in the presence of a Lewis acid such as aluminium trichloride:

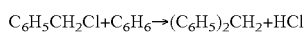

$C_6H_5CH_2Cl+C_6H_6 \rightarrow (C_6H_5)_2CH_2+HCl$

All known above reactions either produce lots of waste and waste water, require expensive reagents or are not practicable in industrial scale.

Object of the present invention is to overcome the disadvantages of the prior art processes, in particular to provide a more efficient and energy saving processes, also more environmentally friendly process, for the manufacture of compounds by Friedel-Crafts reaction, and to provide a beneficially catalyst therefore. Another object of the invention is to provide a Friedel-Crafts reaction, and to provide a beneficially catalyst therefore, which can easily be combined with a fluorination reaction, wherein the fluorination reaction may be prior to the Friedel-Crafts reaction, or may be after the Friedel-Crafts reaction. Herein it is still another object of the invention to provide a catalyst for the Friedel-Crafts reaction which catalyst may be used in both, the Friedel-Crafts reaction and the fluorination reaction.

SUMMARY OF THE INVENTION

The objects of the invention are solved as defined in the claims, and described herein after in detail. In particular, in one aspect, the present invention pertains to a novel environmentally friendly process for the manufacture or synthesis, respectively, of acylated or alkylated aryl compounds, for example, acylated or alkylated benzenes, by the so-called Friedel-Crafts reaction, and a new catalyst therefore. Accordingly, in another aspect, the invention pertains to a novel Friedel-Crafts catalyst or a novel use of a catalyst in a Friedel-Crafts reaction, respectively.

In the context of organic molecules, aryl is any functional group or substituent derived from an aromatic ring, usually an aromatic hydrocarbon, such as phenyl and naphthyl. The term "aryl" is used for the sake of abbreviation or generalization, and "Ar" is used as a placeholder for the aryl group in chemical structure diagrams.

A simple aryl group is phenyl (with the chemical formula $C_6H_5$), a group derived from benzene. The most basic aryl group is phenyl, which is made up of a benzene ring with one hydrogen atom substituted for some substituent, and has the molecular formula $C_6H_5$—. To name compounds containing phenyl groups, the phenyl group can be taken to be the parent hydrocarbon and being represented by the suffix "-benzene". Alternatively, the phenyl group could be treated as the substituent, being described within the name as "phenyl". This is usually done when the group attached to the phenyl group consists of six or more carbon atoms.

The so-called Friedel-Crafts reactions are well known to the persons skilled in the art. For example, Friedel-Crafts reactions are known as a set of reactions developed by Charles Friedel and James Crafts in 1877 to attach substituents to an aromatic ring. Friedel-Crafts reactions are of two main types: alkylation reactions and acylation reactions. Both proceed by electrophilic aromatic substitution.

The Friedel-Crafts alkylation involves the alkylation of an aromatic ring with an alkyl halide using a strong Lewis acid catalyst. With anhydrous ferric chloride as a catalyst, the alkyl group attaches at the former site of the chloride ion. This reaction suffers from the disadvantage that the product is more nucleophilic than the reactant. Consequently, over-alkylation occurs. Furthermore, the reaction is only very useful for tertiary alkylating agents, some secondary alkylating agents, or ones that yield stabilized carbocations (e.g., benzylic ones). In the case of primary alkyl halides, the incipient carbocation ($R^{(+)}$—X—$Al^{(-)}$—$Cl_3$) will undergo a carbocation rearrangement reaction.

The Friedel-Crafts acylation involves the acylation of aromatic rings. Typical acylating agents are acyl chlorides. Typical Lewis acid catalysts are acids and aluminium trichloride. Friedel-Crafts acylation is also possible with acid anhydrides. Reaction conditions are similar to the Friedel-Crafts alkylation. This reaction has several advantages over the alkylation reaction. Due to the electron-withdrawing effect of the carbonyl group, the ketone product is always less reactive than the original molecule, so multiple acylations do not occur. Also, there are no carbocation rearrangements, as the acylium ion is stabilized by a resonance structure in which the positive charge is on the oxygen. The viability of the Friedel-Crafts acylation depends on the stability of the acyl chloride reagent.

A compound of relevance in the context of the present invention is terephthaloyl chloride (TCL, 1,4-benzenedicarbonyl chloride), also known as terephthalic acid dichloride. The preferred IUPAC name is benzene-1,4-dicarbonyl dichloride. Other names are terephthaloyl dichloride, 1,4-benzenedicarbonyl chloride, benzene-1,4-dicarbonyl chloride, terephthalic acid dichloride, terephthaloyl dichloride, p-phthalyl chloride; and a common abbreviation is TCL.

As stated before, all reactions known in the prior art either produce lots of waste and waste water, require expensive reagents or are not practicable in industrial scale.

The disadvantages of the prior art are overcome by the present invention. Hence, this present invention provides a process without waste water, reasonable prices reagents and suitable for industrial scale. More particularly the object is solved by using very cheap clean and easy to make starting materials, and by using $SbHal_5$ based catalyst systems. The invention is also very advantageous even if fluorinated compounds are intended to be prepared, and furthermore, in one embodiment the Friedel-Crafts reaction of the invention optionally is performed in microreactor systems.

The invention, in one aspect, is directed to a process of preparing a compound by Friedel-Crafts reaction, characterized in that the reaction is performed in the presence of an antimony pentahalide catalyst ($SbHal_5$), preferably in the presence of an activated antimony pentahalide catalyst ($SbHal_5$), optionally activated by hydrogen fluoride (HF).

In another aspect, the invention is directed to a use of an antimony pentahalide catalyst ($SbHal_5$), preferably of an activated antimony pentahalide catalyst ($SbHal_5$), optionally activated by hydrogen fluoride (HF), as catalyst in Friedel-Crafts reaction.

In a further aspect, the invention is directed to a use of an antimony pentahalide catalyst ($SbHal_5$), preferably of an activated antimony pentahalide catalyst ($SbHal_5$), optionally activated by hydrogen fluoride (HF), as catalyst in a process of preparing a compound by Friedel-Crafts reaction.

In still a further aspect, the invention is directed to a process or use as defined here before, wherein the Friedel-Crafts reaction is combined with a fluorination reaction, which fluorination reaction may be prior to the Friedel-Crafts reaction, or which fluorination reaction may be after the Friedel-Crafts reaction.

Accordingly, the invention also pertain in one embodiment to a process of preparing a compound by Friedel-Crafts reaction, characterized in that the reaction is performed in the presence of an antimony pentahalide catalyst ($SbHal_5$), preferably in the presence of an activated antimony pentahalide catalyst ($SbHal_5$), optionally activated by hydrogen fluoride (Hf), and wherein the compound prepared is a fluorinated compound.

Surprisingly, it was found that a fluorination catalyst normally used with excess of HF in an industrially beneficial process for preparing fluorobenzenes from halobenzene precursors using HF to form hydrogen halide, in addition can also provide for a beneficial and surprisingly simple use as a Friedel-Crafts catalyst if HF is used in "low" concentration, or HF is absent, and thus provides new opportunities of providing acylated or alkylated compounds as industrially interesting starting materials for the manufacture of compounds by Friedel-Crafts reaction, in a manner that was not known in the prior art before the present invention. The term "low" concentration is defined more particularly herein below in the detailed description of the invention.

Halogenation catalysts and/or fluorination catalysts are well known to those skilled in the field, and preferably in context of the invention, based on Sb, As, Bi, Al, Zn, Fe, Mg, Cr, Ru, Sn, Ti, Co, Ni, preferably on the basis of Sb. More preferably a fluorination catalyst, especially an Sb fluorination catalysts providing the active species $H_2F^+SbF_6^-$, if $SbHal_5$ is kept in an excess of HF for a fluorination step prior or subsequent to the Friedel-Crafts reaction, but wherein in the Friedel-Crafts reaction itself the HF is used in "low" concentration only, e.g. in the ppm-range.

According to the invention, antimony (Sb) is the best and cheapest catalyst, but As and Bi are also possible to be used as fluorination catalyst, and if desired also for the Friedel-Crafts reaction, in the oxidation stage III of the metals, especially in the presence of $SbHal_5$ with a SbHal-III share, or with share of other metal compounds like MHalh compounds, e.g., $AsHal_3$ and $BiHal_3$.

The Friedel-Crafts reaction can be performed in reactors normally used in Friedel-Crafts reactions, but preferably the reactors are resistant to hydrogen fluoride (HF), at least to traces of HF, e.g., in the ppm-range. The Friedel-Crafts reaction may be performed batch-wise process or in a continuous process. Continuous Friedel-Crafts reaction processes may be preferred. In the present invention, in one embodiment of the Friedel-Crafts reaction it is particularly preferred to employ a microreactor.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DESCRIPTION OF THE INVENTION

Figure 1:
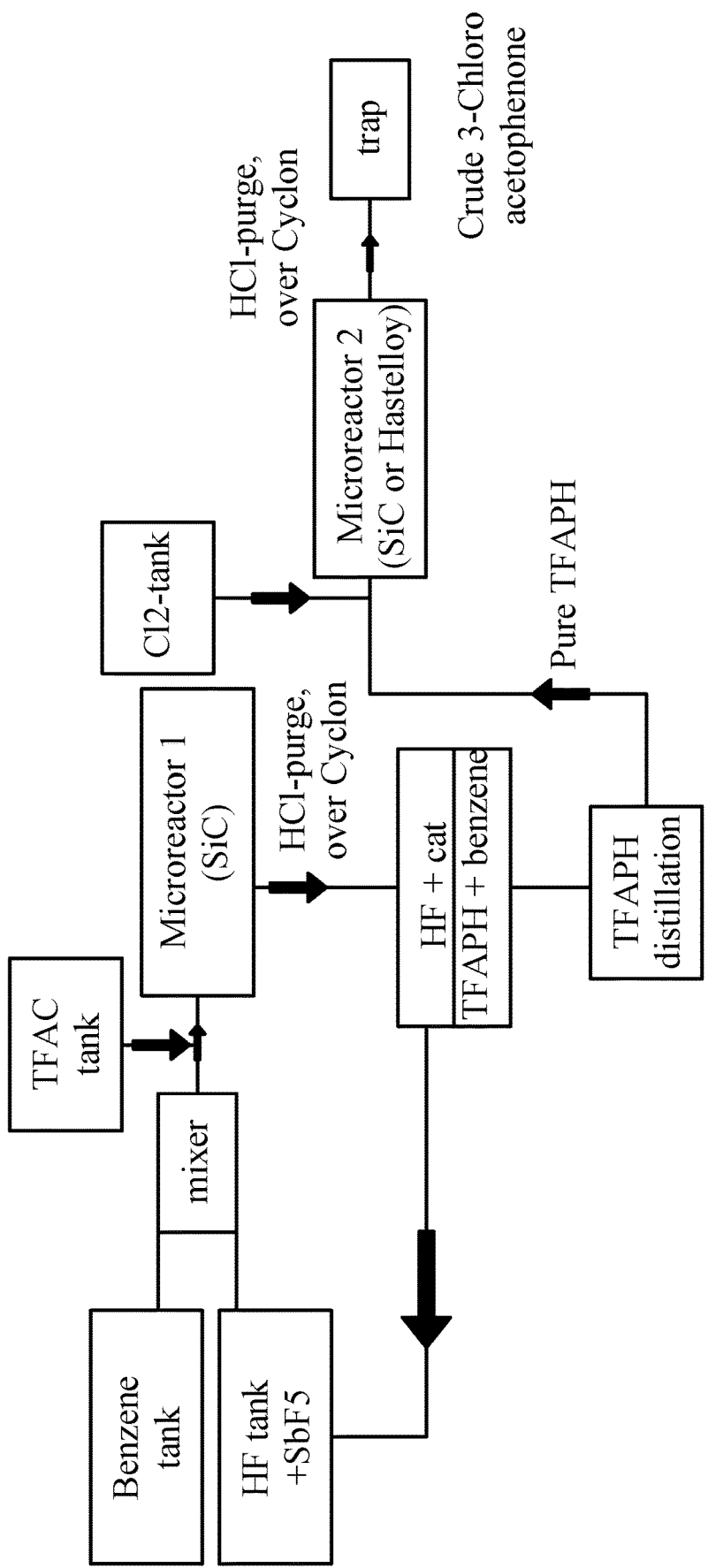
FIG. 1 shows a representative reaction flow scheme by means of the trifluoro acetylation to trifluoroacetophenone and 3-chloro-trifluoroacetophenone.

As briefly described in the Summary of the Invention, and defined in the claims and further detailed by the following description and examples herein, the invention overcomes the shortage of the state of the art.

Thereby, the disadvantages of the prior art are overcome by the present invention. Hence, this present invention provides a process without waste water, reasonable prices reagents and suitable for industrial scale.

More particularly object is solved by using very cheap clean and easy to make starting materials, and by using $SbHal_5$ based catalyst systems. The invention is also very advantageous even if fluorinated compounds are intended to be prepared, and furthermore, in one embodiment the Friedel-Crafts reaction of the invention optionally is performed in microreactor systems; chemistry is given in the following schemes for some options, as examples, but without thereby intending to limit the invention.

Scheme 1: Friedel-Crafts reaction with $CCl_4$ (one pot) batch or continuos (inventive procedure).

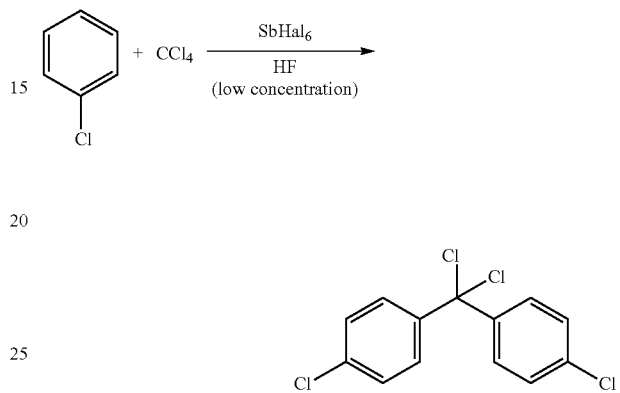

Scheme 2: Friedel-Crafts reaction with 4-chlorobenzoic acid chloride, (one pot) batch or continuous (inventive procedure).

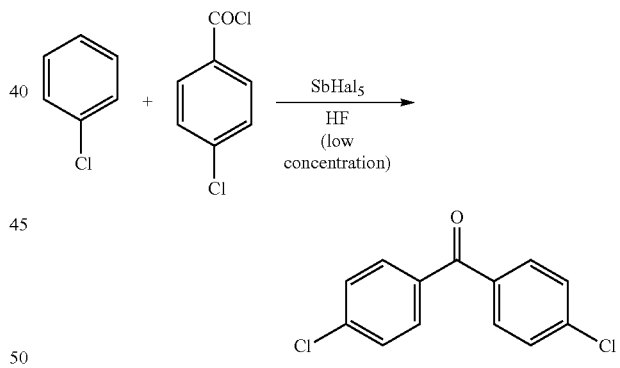

Alternatively to the use of 4-chlorobenzoic acid chloride, according to the invention it is also possible to use of p-chlorophenylboronic acid is another option. The reaction could be done in batch in one or several batch reactors or continuously in microreactor systems. The organic material is preferred separated from catalyst and HF by phase separation. The isolated organic material is subjected to further purification by crystallization (MP: 107° C.). A boronic acid is a compound related to boric acid ($B(OH)_3$) in which one of the three hydroxyl groups is replaced by an alkyl or aryl group. The general structure of a boronic acid is R"—B(OH)$_2$, wherein R" is a substituent. As a compound containing a carbon-boron bond, members of this class thus belong to the larger class of organoboranes. Boronic acids act as Lewis acids.

Scheme 3: Friedel-Crafts reaction with 4-chloro-1-(chloromethyl)benzene, for preparing dichlorodiphenylmethane, batch or continuous (inventive procedure).

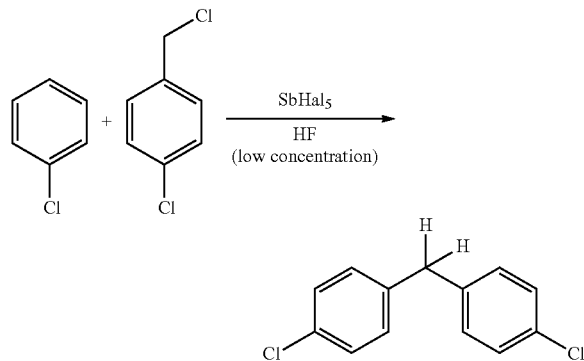

Another interesting molecule as raw material for PAEKs is exemplified by asynthesis which is done again with classical Friedel-Crafts out of terephthaloylchloride and fluorobenzene like described in XiangsuZiyuanLiyong (2011)(2), 1-4, or Hoechst patent No U.S. Pat. No. 5,300,693 and BASF patent No DE3531837. According to the invention, it is also possible to start from chlorobenzene in a Friedel-Crafts reaction (see scheme 4), and then to perform a fluorination step to convert the dichloro compound obtained to the difluoro compound.

Scheme 4: Conversion of terephtaloylchloride with chlorobenzene by Friedel-Crafts reaction with, batch or continuous (inventive procedure).

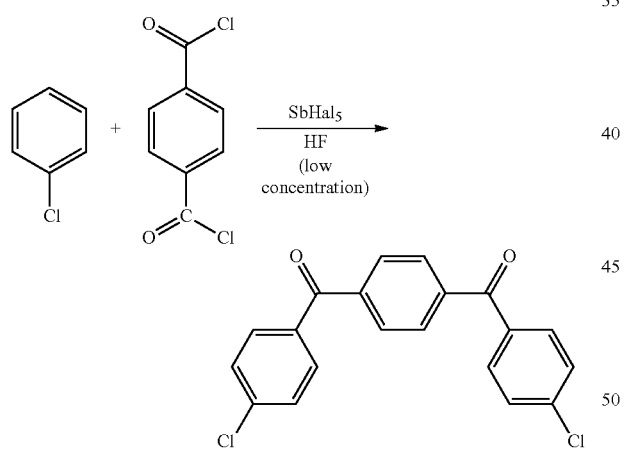

If alternatively fluorobenzene is used instead of chlorobenzene, just the Friedel-Crafts step is applied, and is as claimed in present invention, and no additional fluorination step is necessary, because the difluoro compound is directly obtained.

All the inventive reactions can be performed in batch reactors (autoclaves) either lined with HDPTFE or SiC-equipment or continuously in microreactors or plug flow reactors. A series of STRs ("stirred vessels") is also possible, but plug flow and microreactor are more advantageous.

Of course, the Friedel-Crafts reaction of 4-chlorobenzoylchloride, 4-chlorobenzylchloride and terephtaloylchloride could be performed by known methods, other than the inventive method disclosed herein, but when using the inventive process described herein, additional separation steps are avoided and the product yield is increased.

Scheme 5: Acylation ofchlorobenzene according to the invention.

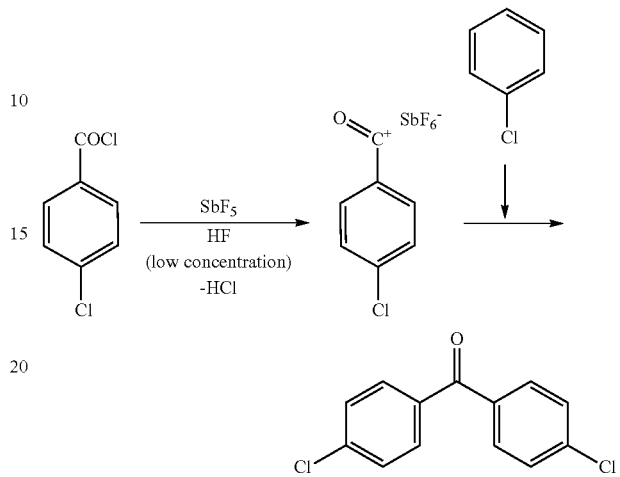

Scheme 6: Acylation of fluorobenzene according to the invention.

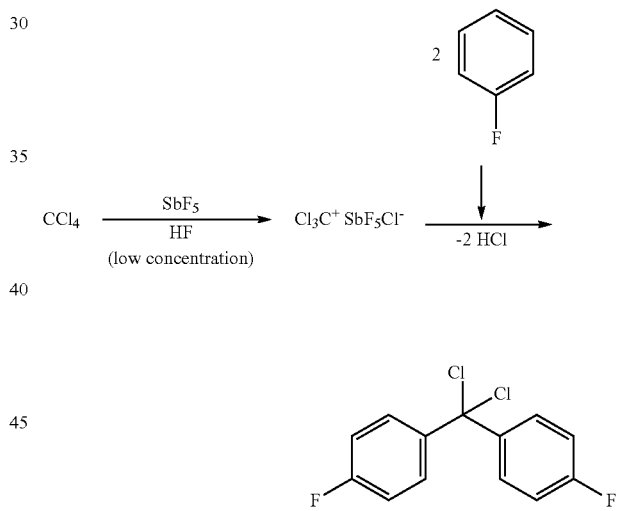

Scheme 7: Preparation of 4,4'-difluorophenylmethane by acylation of chlorobenzene according to the invention.

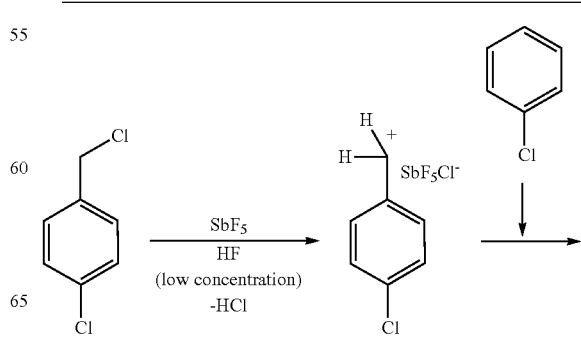

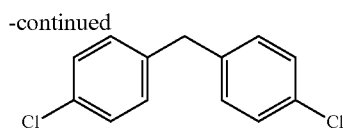

In one aspect, the present invention pertains to a novel environmentally friendly process for the manufacture or synthesis, respectively, of acylated or alkylated aryl compounds, for example, acylated or alkylated benzenes, by the so-called Friedel-Crafts reaction, and a new catalyst therefore. The invention relates to a new process for performing the Friedel-Crafts reaction, and especially wherein said Friedel-Crafts reaction, as defined in the claims and as further described herein, relates to an environmentally friendly production of acylated or alkylated aryl compounds. In another aspect, the invention pertains to a novel Friedel-Crafts catalyst or a novel use of a catalyst in a Friedel-Crafts reaction, respectively.

Thus, the present invention overcomes the disadvantages of the prior art processes, and in a surprisingly simple and beneficial manner, and as compared to the prior art processes, in particular, the invention provides a more efficient and energy saving processes, and also provides a more environmentally friendly process, for performing a Friedel-Crafts reaction.

The Friedel-Crafts reaction can be performed in reactors normally used in Friedel-Crafts reactions, but preferably the reactors are resistant to hydrogen fluoride (HF), at least to traces of HF, e.g., in the ppm-range. The Friedel-Crafts reaction may be performed batch-wise process or in a continuous process. Continuous Friedel-Crafts reaction processes may be preferred. In the present invention, in one embodiment of the Friedel-Crafts reaction it is particularly preferred to employ a microreactor.

The Catalyst:

Surprisingly, it was found that a fluorination catalyst normally used with excess of HF in an industrially beneficial process for preparing fluorobenzenes from halobenzene precursors using HF to form hydrogen halide, in addition can also provide for a beneficial and surprisingly simple use as a Friedel-Crafts catalyst if used in "low" concentration, and thus provides new opportunities of providing acylated or alkylated compounds as industrially interesting starting materials for the manufacture of compounds by Friedel-Crafts reaction, in a manner that was not known in the prior art before the present invention.

The processes of the invention employ a halogenation catalyst, preferably a fluorination catalyst which also can be—but not exclusively—a so called Lewis acid. Halogenation is a chemical reaction that involves the addition of one or more halogens to a compound or material. The pathway and stoichiometry of halogenation depends on the structural features and functional groups of the organic substrate, as well as on the specific halogen. Inorganic compounds such as metals also undergo halogenation. Fluorination is a halogenation wherein F (fluorine) is the halogen introduced into a compound or material. Halogenation and/or fluorination are well known to those skilled in the art, as well as the halogenation catalysts and/or fluorination catalysts involved in these reactions. For example, the addition of halogens, e.g. chlorine and/or fluorine, to alkenes proceeds via intermediate halonium ions as an active species, wherein "halonium ion" in organic chemistry denotes any onium compound (ion) containing a halogen atom, e.g. herein in context of the invention a fluorine atom, carrying a positive charge.

Halogenation catalysts and/or fluorination catalysts are well known to those skilled in the field, and preferably in context of the invention, based on Sb, As, Bi, Al, Zn, Fe, Mg, Cr, Ru, Sn, Ti, Co, Ni, preferably on the basis of Sb. More preferably a fluorination catalyst, especially an Sb fluorination catalysts providing the active species $H_2F^+SbF_6^-$, if $SbHal_5$ is kept in an excess of HF for a fluorination step prior or subsequent to the Friedel-Crafts reaction, but wherein in the Friedel-Crafts reaction itself the HF is used in "low" concentration only, e.g. in the ppm-range.

According to the invention, antimony (Sb) is the best and cheapest catalyst, but As and Bi are also possible to be used as fluorination catalyst, and if desired also for the Friedel-Crafts reaction, in the oxidation stage III of the metals, especially in the presence of $SbHal_5$ with a SbHal-III share, or with share of other metal compounds like $MHal_3$ compounds, e.g., $AsHal_3$ and $BiHal_3$.

For example, in one aspect of the invention, involving also a fluorination reaction, the application of antimony (Sb) catalysts for the manufacture of nuclear fluorinated aromatic systems ("fluorobenzenes") is new and advantageous. The catalyst, for example, is $SbF_5$ in HF, made naturally from $SbCl_5$. At the beginning of the reaction with fresh catalyst, of course, one or two chlorine atoms on the antimony (Sb) of the catalyst can be exchanged, and all Chlorine atoms will be exchanged after a certain time of performing the fluorination.

So far, for example, fluorobenzene and derivatives are industrially made with BalzSchiemann or Sandmeyer reaction. These two types of reactions are chemically very good but disadvantageously cause a lot of waste, and also in the form of very toxic wastewater. For this reason, even entire chemical plants are currently closed, e.g., in China, and many companies worldwide are now without reliable and environmentally acceptable fluorobenzene sources. Same or similar problems described here by example of fluorobenzene may generally be also applicable to the preparation of other fluorinated aromatic and heteroaromatic compounds, e.g., such as used as building blocks in the pharmaceutical and agrochemical field.

Figure 2:
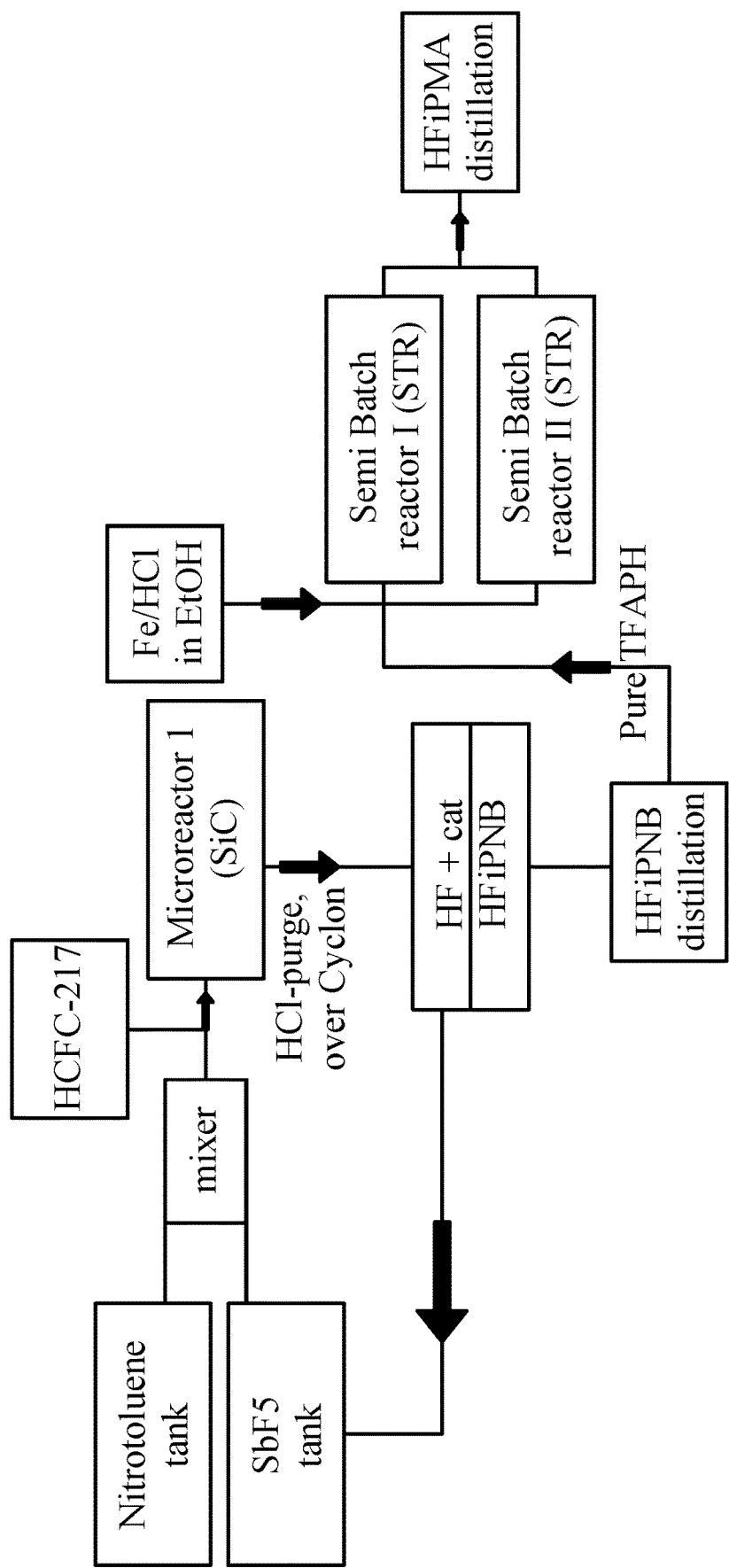
FIG. 2 shows a representative reaction flow scheme by means of heptafluoroisopropyl-3-methyl nitrobenzene.

Particular examples related to the use of the Friedel-Crafts reaction, including the alkylation and the acylation are shown in the Examples 4, and FIG. 1, and in the Examples 5, and FIG. 2, which examples each are incorporated into this description part of the invention by reference in its entirety and entire breadth.

FIG. 1:

FIG. 1 shows a representative reaction flow scheme by means of the trifluoro acetylation to trifluoroacetophenone and 3-chloro-trifluoroacetophenone.

FIG. 2:

FIG. 2 shows a representative reaction flow scheme by means of heptafluoroisopropyl-3-methyl nitrobenzene.

The chemical novelty and concept of the invention is that a new Friedel-Crafts process with use of halogenation catalysts is proposed, that also may be combined in a beneficial manner with fluorination processes, in particular without need of changing the catalyst which according to the present invention may be used in both, the Friedel-Crafts reaction and the fluorination reaction. For example, in preferred embodiments antimony (Sb) halides normally used as halogenation catalysts, are used in the invention and as described herein as a Friedel-Crafts catalyst when the concentration of HF, which may be used for activating the catalyst, is "low" in the Friedel-Crafts reaction. In an alternative of the invention, HF may be even absent in the Friedel-Crafts reaction. Thus, according to the present invention a new Friedel-Crafts reaction is provided which in itself is environmentally friendly, and which easily can be combined, for example, with fluorination processes, that then in turnare used in manufacturing processes to catalytically produce, e.g., fluorobenzene and derivatives thereof, in particular without any (at least not any significant) waste by-products. Such process of flourination, for example, then only produces marketable hydrogen chloride (HCl) grades.

However, if trifluoroacetic acid is used as the Friedel-Crafts reagent, then there is no need to keep the concentration of HF, which may be used for activating the catalyst, is "low" in the Friedel-Crafts reaction, and higher amounts of HF, e.g. even up to 5-times or 10-times molar ratio to the antimony (Sb) are allowed, especially if there are only other compounds involved in the reaction which are inert to fluorination. In such case up to substantial amounts of HF may be present.

The Reactors:

In addition to the above, according to one aspect of the invention, also a plant engineering invention is provided, as used in the process invention and described herein, pertaining to the optional, and in some embodiments of the process invention, the process even preferred implementation in microreactors.

As to the term "microreactor": A "microreactor" or "microstructured reactor" or "microchannel reactor", in one embodiment of the invention, is a device in which chemical reactions take place in a confinement with typical lateral dimensions of about ≤1 mm; an example of a typical form of such confinement are microchannels. Generally, in the context of the invention, the term "microreactor": A "microreactor" or "microstructured reactor" or "microchannel reactor", denotes a device in which chemical reactions take place in a confinement with typical lateral dimensions of about ≤5 mm.

Microreactors are studied in the field of micro process engineering, together with other devices (such as micro heat exchangers) in which physical processes occur. The microreactor is usually a continuous flow reactor (contrast with/to a batch reactor). Microreactors offer many advantages over conventional scale reactors, including vast improvements in energy efficiency, reaction speed and yield, safety, reliability, scalability, on-site/on-demand production, and a much finer degree of process control.

Microreactors are used in "flow chemistry" to perform chemical reactions.

In flow chemistry, wherein often microreactors are used, a chemical reaction is run in a continuously flowing stream rather than in batch production. Batch production is a technique used in manufacturing, in which the object in question is created stage by stage over a series of workstations, and different batches of products are made. Together with job production (one-off production) and mass production (flow production or continuous production) it is one of the three main production methods. In contrast, in flow chemistry the chemical reaction is run in a continuously flowing stream, wherein pumps move fluid into a tube, and where tubes join one another, the fluids contact one another. If these fluids are reactive, a reaction takes place. Flow chemistry is a well-established technique for use at a large scale when manufacturing large quantities of a given material. However, the term has only been coined recently for its application on a laboratory scale.

Continuous flow reactors, e.g. such as used as microreactor, are typically tube like and manufactured from non-reactive materials, such known in the prior art and depending on the specific purpose and nature of possibly aggressive agents and/or reactants. Mixing methods include diffusion alone, e.g. if the diameter of the reactor is narrow, e.g. <1 mm, such as in microreactors, and static mixers. Continuous flow reactors allow good control over reaction conditions including heat transfer, time and mixing. The residence time of the reagents in the reactor, i.e. the amount of time that the reaction is heated or cooled, is calculated from the volume of the reactor and the flow rate through it: Residence time=Reactor Volume/Flow Rate. Therefore, to achieve a longer residence time, reagents can be pumped more slowly, just a larger volume reactor can be used and/or even several microreactors can be placed in series, optionally just having some cylinders in between for increasing residence time if necessary for completion of reaction steps. In this later case, cyclones after each microreactor help to let formed HCl to escape and to positively influence the reaction performance. Production rates can vary from milliliters per minute to liters per hour.

Some examples of flow reactors are spinning disk reactors (Colin Ramshaw); spinning tube reactors; multi-cell flow reactors; oscillatory flow reactors; microreactors; hex reactors; and aspirator reactors. In an aspirator reactor a pump propels one reagent, which causes a reactant to be sucked in. Also to be mentioned are plug flow reactors and tubular flow reactors.

In the present invention, in one embodiment it is particularly preferred to employ a microreactor.

The Combination of Friedel-Crafts Reaction and Fluorination Reaction:

Antimony pentafluoride in an excess of anhydrous HF gives the superacid $H_2F^+SbF_6^-$, a strongly nucleophilic fluoride atom. It has been found that highly fluorinated $SbF_5$ in anhydrous HF as a solvent fluorinates benzenes and even deactivated halogenobenzenes in a nucleophilic exchange reaction, especially chlorobenzene, and bromobenzene and derivatives, also very deactivated precursors can be used as starting materials. This fluorination reaction takes place in the presence of excess of HF. Surprisingly, now it was also found the catalyst used for fluorination in the presence of HF, can also be used as a Friedel-Crafts catalyst if no HF is present, or if HF is present only in "low" concentration.

Sb-pentahalides, as such in inert solvents such as perfluorinated solvents, would function mainly as a Lewis acid and, upon hydrolysis, would provide phenols and biphenyls. Only if $SbHal_5$ undergoes a reduction to $SbHal_3$ a halogenation is possible, but not catalytically. Reactions of antimony pentafluorides with chlorobenzenes are unknown, and the skilled person would normally expect Friedel-Crafts products or just a polymerisation, decomposition or formation of undefined products and oligomers. In Journal of the Chemical Society, Perkin Transactions 2: Physical Organic Chemistry (1997) (11), 2301-2306 a reaction of chlorobenzene with phenyl disulfide is described, here $SbCl_5$ acts as a Friedel-Crafts catalyst, not as a halogenating reagent. In Theoretical and Experimental Chemistry (2011), 47 (2), 123-128, $SbCl_5$ is part of a chlorinating reagent for the scientific production of dichlorobenzene together with crown ethers and chlorine gas, but this may not be suitable as an industrial process.

However, if the fluorination reaction is carried out in anhydrous HF as solvent and in a temperature range starting at slightly higher temperature than ambient temperature, the nucleophilic halogen-fluorine exchange takes place in very good yields and rapid reaction rates because in (excess) HF, a change of functionality of the antimony pentahalide from a Friedel-Crafts catalyst function to the nucleophilic fluorination functionality, or to the fluorination agent takes place, and namely in the form the super-acidic very strongly nucleophilic fluorine anion (F⁻) which is offered to, e.g., the chlorobenzene as a reaction partner, and preferably to produce a nuclear fluorinated fluorobenzene. For example, in case of more active, the fluorination can take place already at a temperature starting from of about 40° C. But slightly higher temperatures than the said 40° C., of course, are also advantageous for bringing HCl, once formed, into the gas phase, and thereby the fluorination reaction is accelerated. Since antimony (Sb) in oxidation stage V (i.e., Sb-V) decomposes to Sb-III at a temperature starting from about 130° C., and even without any reactants being present, the upper reaction temperature should not be too high. Accordingly, in one embodiment, the temperature of the fluorination reaction is in the range of from about 40° C. to 130° C. In a preferred embodiment, the temperature of the fluorination reaction is in the range of from about 40° C. to 110° C., more preferably in the range of from about 50° C. to 110° C., even more preferably in the range of from about 60° C. to 110° C., and still more preferably in the range of from about 70° C. to 110° C. Most preferably, the temperature of the fluorination reaction is in the range of from about 80° C. to 110° C., which is the optimal temperature range. The preceding applies to all chlorobenzenes and chlorobenzene derivatives, including chlorobenzenes with chemically deactivating substituents such as other halogens or strong-pulling substituents such as cyano or nitro groups. Similarly, this applies to the manufacture other nuclear fluorinated aromatics, if such other nuclear fluorinated aromatics shall be produced from the corresponding nuclear chlorinated aromatics as the starting material. For example, but without wishing to be bound to a theory, in nucleophilic reactions, substituents such as CN and $NO_2$, which otherwise normally are deactivating, herein increase the reactivity towards nucleophiles, because electrons are attracted to the substituent, and thus the delta+ is increased at other positions and in the aromatic ring.

In the following, the general embodiments of the invention shall be described in more detail, to illustrate breadth of the invention that is duly explored and based a skilled person's educated guess, and thus derivable from the more specific embodiments described further below.

The invention, in a first embodiment, is directed to a process of preparing a compound by Friedel-Crafts reaction, characterized in that the reaction is performed in the presence of an antimony pentahalide catalyst ($SbHal_5$), preferably in the presence of an activated antimony pentahalide catalyst ($SbHal_5$), optionally activated by hydrogen fluoride (Hf).

In a second embodiment, the invention is directed to a use of an antimony pentahalide catalyst ($SbHal_5$), preferably of an activated antimony pentahalide catalyst ($SbHal_5$), optionally activated by hydrogen fluoride (HF), as catalyst in Friedel-Crafts reaction.

In a third embodiment, the invention is directed to a use of an antimony pentahalide catalyst ($SbHal_5$), preferably of an activated antimony pentahalide catalyst ($SbHal_5$), optionally activated by hydrogen fluoride (HF), as catalyst in a process of preparing a compound by Friedel-Crafts reaction.

In a forth embodiment, the invention is directed to a process or use as defined here before, wherein the Friedel-Crafts reaction is combined with a fluorination reaction, which fluorination reaction may be prior to the Friedel-Crafts reaction, or which fluorination reaction may be after the Friedel-Crafts reaction.

Accordingly, the invention also pertains in one embodiment to a process of preparing a compound by Friedel-Crafts reaction, characterized in that the reaction is performed in the presence of an antimony pentahalide catalyst ($SbHal_5$), preferably in the presence of an activated antimony pentahalide catalyst ($SbHal_5$), optionally activated by hydrogen fluoride (HF), and wherein the compound prepared is a fluorinated compound.

The invention also pertains in one embodiment to a process of preparing a compound as described above, in particular a compound comprising one or more aromatic rings, by Friedel-Crafts reaction, characterized in that an aromatic ring of a starting material compound is reacted with a Friedel-Crafts reagent in the presence of an antimony pentahalide catalyst ($SbHal_5$), preferably in the presence of an activated antimony pentahalide catalyst ($SbHal_5$), optionally activated by hydrogen fluoride (HF), preferably wherein the compound prepared is a fluorinated compound.

The invention also pertains in one embodiment to a process of preparing a compound as described above, wherein a starting material compound is selected from compounds having the formula (I):

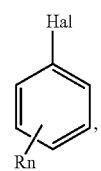

(I)

wherein, in principle, the residue Rn can be any substituent that is "inert" under the reaction conditions of fluorination and Friedel-Crafts reaction; including, e.g., ring systems, and including inert heterocycles are possible to be used in the invention, but preferably wherein Rn independently denotes one or more substituents selected from the group consisting of hydrogen (H), nitrogendioxide ($NO_2$), and if present preferably only one Rn group is nitrogendioxide ($NO_2$), halogen, preferably fluorine (F) or chlorine (Cl), a substituted or unsubstituted $C_1$-$C_4$ alkyl, a substituted or unsubstituted $C_1$-$C_4$ alkoxy, preferably a difluoralkoxy or trifluoralkoxy group, more preferably a difluormethoxy or trifluormethoxy group, a substituted or unsubstituted $C_1$-$C_4$ haloalkyl wherein the halogen is selected from fluorine (F), chlorine (Cl), bromine (Br) or Iodine (I), a substituted or unsubstituted $C_1$-$C_4$ haloalkoxy wherein the halogen is selected from fluorine (F), chlorine (Cl), bromine (Br) or Iodine (I); and Hal denotes a halogen selected from fluorine (F), chlorine (Cl), bromine (Br) or Iodine (I); preferably fluorine (F) or chlorine (Cl); or Hal is absent, i.e., at the position of Hal there is hydrogen (H).

In an embodiment, wherein Hal is absent, i.e, at the position of Hal there is hydrogen (H), Rn represents a substituent $R^1n$ and one to five, preferably one, substituents $R^2n$, wherein $R^1n$ denotes hydrogen (H) or nitrogen dioxide (NO2), and $R^2n$ denotes hydrogen (H), fluorine (F), a substituted or unsubstituted $C_1$-$C_4$ alkyl, a substituted or unsubstituted $C_1$-$C_4$ alkoxy, preferably a difluoralkoxy or trifluoralkoxy group, more preferably a difluormethoxy or trifluormethoxy group, a substituted or unsubstituted $C_1$-$C_4$ haloalkyl wherein the halogen is selected from fluorine (F) and/or chlorine (Cl), preferably fluorine (F), a substituted or unsubstituted $C_1$-$C_4$ haloalkoxy wherein the halogen is selected from fluorine (F) and/or chlorine (Cl), preferably fluorine (F).

For example, in such embodiment Hal is absent, i.e., at the position of Hal there is hydrogen (H), Rn represents a single substituent $R^1n$ and a single substituent $R^2n$, wherein $R^1n$ denotes hydrogen (H) or nitrogen dioxide (NO2), and $R^2n$ denotes hydrogen (H), fluorine (F) or a substituted or unsubstituted $C_1$-$C_2$ alkyl, and preferably $R^2n$ denotes hydrogen (H) or methyl. Representative examples are benzene and 2-methyl-nitrobenzene (m-nitrotoluene).

For example, in the process of preparing a compound as described above, the starting material compound is selected from compounds having the formula (I) as defined above, wherein
  Rn independently denotes one or more substituents selected from the group consisting of hydrogen (H), fluorine (F), chlorine (Cl), a substituted or unsubstituted methyl or ethyl group, preferably a methyl group; and
  Hal denotes a halogen selected from fluorine (F) or chlorine (Cl), preferably chlorine (Cl).

For example, in the process of preparing a compound as described above, the starting material compound is selected from the group of compounds consisting of compounds wherein one of Rn, preferably a Rn in para-position (4-Rn), is fluorine (F) or chlorine (Cl), and the others of Rn are hydrogen, and Hal is fluorine (F) or chlorine (Cl); preferably wherein the starting material compound is selected from the group of compounds consisting of the compounds chlorobenzene, dichlorobenzene, preferably 1,4-dichlorobenzene, fluorobenzene, and difluorobenzene, preferably 1,4-difluorobenzene, more preferably wherein the starting material compound is selected from the group of compounds consisting of the compounds chlorobenzene and fluorobenzene.

The invention also pertains in one embodiment to a process of preparing a compound as defined above, wherein a Friedel-Crafts reagent is selected from one of the compounds either having the formula (II), the formula (III), or the formula (IV):

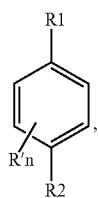

(II)

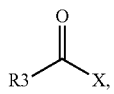

(III)

R4-Y, (IV)

Wherein in the formula (II):
R'n independently denotes one or more substituents selected from the group consisting of hydrogen (H), nitrogendioxide (NO$_2$), and if present preferably only one R'n group is nitrogen dioxide (NO$_2$), halogen, preferably fluorine (F) or chlorine (Cl), a substituted or unsubstituted $C_1$-$C_4$ alkyl, a substituted or unsubstituted $C_1$-$C_4$ alkoxy, preferably a difluoralkoxy or trifluoralkoxy group, more preferably a difluoromethoxy or trifluormethoxy group, a substituted or unsubstituted $C_1$-$C_4$ haloalkyl wherein the halogen is selected from fluorine (F), chlorine (Cl), bromine (Br) or Iodine (I), a substituted or unsubstituted $C_1$-$C_4$ haloalkoxy wherein the halogen (Hal) is selected from fluorine (F), chlorine (Cl), bromine (Br) or Iodine (I); and R1 and R2 independently from each other denote a hydrogen, a tri-halogeno methyl group (—CHal$_3$), a halogeno carbonyl group (—(C═O)Hal) or a halogeno methyl group (—CH$_2$Hal), and at least one of R1 and R2 is a tri-halogeno methyl group (—CHal$_3$), a halogeno carbonyl group (—(C═O)Hal) or a halogeno methyl group (—CH$_2$Hal), and wherein each halogen (Hal) is selected from fluorine (F), chlorine (Cl), bromine (Br) or Iodine (I), preferably wherein the halogen (Hal) is selected from fluorine (F) and chlorine (Cl), more preferably wherein the halogen (Hal) is chlorine (Cl); a boronic acid group;

wherein in the formula (III):
R3 independently denotes a substituted or unsubstituted $C_1$-$C_4$ alkyl, a substituted or unsubstituted $C_1$-$C_4$ haloalkyl wherein the halogen is selected from fluorine (F) and/or, chlorine, preferably wherein R3 is a $C_1$-$C_4$-perfluoroalkyl or is a $C_1$-$C_4$-chlorofluoroalkyl, and X represents a halogen selected from fluorine (F), chlorine (Cl), bromine (Br) or Iodine (I), preferably wherein the halogen is selected from fluorine (F) or chlorine (Cl), more preferably wherein the halogen is chlorine (Cl); or X represents an anhydride group —O—(C═O)—R'3, wherein R'3 independently has the meaning as defined for R3, preferably wherein R'3 and R3 are the same;
  preferably wherein in an embodiment, wherein R3 is a $C_1$-$C_4$-perfluoroalkyl or is a $C_1$-$C_4$-chlorofluoroalkyl, and X is chlorine (Cl), for example, a representative Friedel-Crafts reagent is trifluoroacetylchloride; or wherein R3 is a $C_1$-$C_4$-perfluoroalkyl or is a $C_1$-$C_4$-chlorofluoroalkyl, and X is an anhydride group —O—(C═O)—R'3; a representative Friedel-Crafts reagent is trifluoroacetic acid anhydride, the anhydrides of chlorodifluoro acetic acid or of difluorchloro acetic acid;

wherein in the formula (IV):
R4 independently denotes a substituted or unsubstituted $C_1$-$C_4$ alkyl, a substituted or unsubstituted $C_1$-$C_4$ haloalkyl wherein the halogen is selected from fluorine (F) and/or chlorine, preferably wherein R4 is a $C_1$-$C_4$-perfluoroalkyl or is a $C_1$-$C_4$-chlorofluoroalkyl, and Y represents a halogen, which may be at any position in R4, and wherein the selected from chlorine (Cl), bromine (Br) or Iodine (I), preferably wherein the halogen is chlorine (Cl);
  preferably wherein in an embodiment, wherein R4 is a $C_1$-$C_4$-perfluoroalkyl and Y is chlorine (Cl), for example, a representative Friedel-Crafts reagent is heptafluoropropyl chloride.

A boronic acid is a compound related to boric acid (B(OH)$_3$) in which one of the three hydroxyl groups is replaced by an alkyl or aryl group. The general structure of a boronic acid is R"—B(OH)$_2$, wherein R" is a substituent. As a compound containing a carbon-boron bond, members of this class thus belong to the larger class of organoboranes. Boronic acids act as Lewis acids.

In principle, the residue R'n can be any substituent that is "inert" under the reaction conditions of fluorination and Friedel-Crafts reaction; including, e.g., ring systems, and including inert heterocycles are possible to be used in the invention.

For example, in the process of preparing a compound as defined above, a Friedel-Crafts reagent is selected from compounds having the formula (II) as defined herein above, wherein
R'n independently denotes one or more substituents selected from the group consisting of hydrogen (H), fluorine (F), chlorine (Cl), a substituted or unsubstituted methyl or ethyl group, preferably a methyl group; and
R1 and R2 independently from each other denote a hydrogen, a trichloromethyl group (—$CCl_3$), a carbonyl chloride group (—(C=O)Cl) or a chloromethyl group (—$CH_2Cl$), and at least one of R1 and R2 is a trichloromethyl group (—$CCl_3$), a carbonyl chloride group (—(C=O)Cl) or a chloromethyl group (—$CH_2Cl$), or a boronic acid group.

For example, in the process of preparing a compound as defined above, the Friedel-Crafts reagent is selected from compounds having the formula (II) as defined in claim 7, wherein R1 and R2 independently from each other denote a hydrogen, a carbonyl chloride group (—(C=O)Cl) or a chloromethyl group (—$CH_2Cl$), and at least one of R1 and R2 is a carbonyl chloride group (—(C=O)Cl) or a chloromethyl group (—$CH_2Cl$), or a boronic acid group.

For example, in the process of preparing a compound as defined above, the Friedel-Crafts reagent is selected from the group compounds consisting of chlorobenzoic acid chloride, fluorobenzoic acid chloride, (4-chlorophenyl) boronic acid, benzene-dicarbonyl dichloride and chloromethyl chlorobenzene, preferably 4-chlorobenzoic acid chloride, benzene-1,4-dicarbonyl dichloride, and 4-(chloromethyl)-1-chlorobenzene.

For example, in the process of preparing a compound as defined above, the Friedel-Crafts reagent is selected from compounds having the formula (II) as defined herein before, wherein the tri-halogeno methyl group (—$CHal_3$), or the trichloromethyl group (—$CCl_3$), respectively, is prepared in situ from tetrahalogenomethane in the process as defined above, or is prepared in situ from tetrachloromethane in the process as defined above, in the presence of the starting material compound.

For example, in the process of preparing a compound as defined above, the Friedel-Crafts reagent is prepared in situ from tetrahalogenomethane, and the starting material compound is chlorobenzene and fluorobenzene.

The invention also pertains in one embodiment to a process of preparing a compound by Friedel-Crafts reaction as defined above, characterized in that
(a) the reaction is performed in the presence of an antimony pentahalide catalyst ($SbHal_5$), preferably in the presence of an activated antimony pentahalide catalyst ($SbHal_5$), optionally activated by hydrogen fluoride (HF), and in that the process is a continuous process; or
(b) in case the process comprises two or more steps, comprising
(b1) as one of the steps a Friedel-Crafts reaction, wherein a starting material compound is reacted with a Friedel-Crafts reagent, in the presence of an antimony pentahalide catalyst ($SbHal_5$), optionally activated by hydrogen fluoride (Hf) present in low concentration, and
(b2) one of the steps a fluorination reaction, wherein a compound is reacted in the presence of an antimony pentahalide catalyst ($SbHal_5$) with hydrogen fluoride (HF) present in excess concentration,
wherein at least one of the said steps (b1) and (b2) is a continuous process,
preferably wherein of the said steps at least (b2) the step of a fluorination reaction is a continuous process,
more preferably wherein of the said steps (b1) of Friedel-Crafts reaction, and (b2) of fluorination reaction both are a continuous process.

The invention also pertains in one embodiment to a process of preparing a compound as defined above, wherein at least one of the said continuous processes of the said steps (b1) and (b2),
preferably wherein of the said steps at least (b2) the step of a fluorination reaction is a continuous process,
more preferably wherein of the said steps (b1) of Friedel-Crafts reaction, and (b2) of fluorination reaction both are a continuous process,
wherein the continuous process is performed in at least one continuous flow reactor with upper lateral dimensions of about ≤5 mm, or of about ≤4 mm, preferably in at least one microreactor;
most preferably wherein of the said steps at least (b2) the step of a fluorination reaction is a continuous process in at least one microreactor under one or more of the following conditions:
flow rate: of from about 10 ml/h up to about 400 l/h;
temperature: of from about 30° C. up to about 150° C.;
pressure: of from about 4 bar up to about 50 bar;
residence time: of from about 1 second, preferably from about 1 minute, up to about 60 minutes.

For example, in the process of preparing a compound as defined above, at least one of the said continuous flow reactors, preferably at least one of the microreactors, independently is a SiC-continuous flow reactor, preferably independently is anSiC-microreactor.

For example, in the process of preparing a compound as defined above, the process comprises in a further step (b3) purifying and/or isolating the targeted compound obtained in a process of preparing a compound as defined above, to yield the said purified and/or isolated compound.

For example, in the process as defined above, in the further step (b3) the purifying and/or isolating of the targeted compound comprises or consists of a phase separation method, preferably wherein in the further step (b3) the purifying and/or isolating of the targeted compound does not comprise a distillation to yield purified and/or isolated targeted compound.

The Concentration of HF:

The meaning of the term "low", in the context of the Friedel-Crafts reaction, is a concentration of at least an amount of traces of HF, e.g., traces of HF in the range of from about 0.1 ppm to about 100 ppm. Such amounts in ppm-traces of HF can be employed if, for example, the starting material, a reaction partner, or the desired product is used as the solvent. Alternatively, an inert solvent can also be used, e.g., hexafluorobenzene or perfluorodecaline can be used as solvents. In some embodiments the HF-concentration may even be as low as about zero, or even zero (1F is absent).

For the fluorination at the benzene nucleus one needs then of course "excess" HF so that nucleophilic fluorinating $H_2F^+SbF_6^-$-species forms.

Regarding the excess of HF, there is no method of analysis required to determine the amount of $H_2F^+SbF_6^-$-species, but it can be estimated that starting at about a 2-times molar excess of HF as compared to the molar amount of Sb can be regarded as the lower value required as the lower limit already forms sufficient content of the $H_2F^+SbF_6^-$-species in the reaction mixture. The upper limit is not critical, and can be up to an infinite surplus, however for practical reason, of course, the upper limit of HF is chosen such that it is adapted to the molar amount of fluorine needed in the fluorination reaction. Accordingly, in an embodiment of the fluorination reaction, the upper limit of HF can be up to about 40-times molar excess of HF as compared to the molar amount of Sb. In another embodiment of the fluorination reaction, the upper limit of HF can be up to about 30-times molar excess, preferably the upper limit of HF can be up to about 20-times molar excess, more preferably the upper limit of HF can be up to about 10-times molar excess, of HF, each as compared to the molar amount of Sb.

Thus, the excess HF-concentration in the fluorination reaction, as compared to the molar amount of Sb, is in the range of about 2-times excess of HF up to about 40-times molar excess of HF. In another embodiment of the fluorination reaction, the excess HF-concentration in the fluorination reaction, each as compared to the molar amount of Sb, is in the range of about 2-times excess of HF up to a about 30-times molar excess of HF, preferably is in the range of about 2-times excess of HF up to about 20-times molar excess, more preferably is in the range of about 2-times excess of HF up to about 10-times molar excess.

In a particular embodiment of the process of preparing a compound according to the invention, at least one of the said continuous flow reactors, preferably at least one of the microreactors, independently is a SiC-continuous flow reactor, preferably independently is anSiC-microreactor.

In a particular embodiment of the process of preparing a compound according the invention, in the fluorination reaction the catalyst is a halogenation catalyst, preferably a fluorination catalyst, on the basis of Sb, As, Bi, Al, Zn, Fe, Mg, Cr, Ru, Sn, Ti, Co, Ni, preferably on the basis of Sb, more preferably a fluorination catalyst wherein the fluorination catalyst is selected from the group consisting of Sb fluorination catalysts providing the active species $H_2F^+SbF_6^-$.

Preferably, in this particular embodiment of the process of preparing a compound according to the invention, in the fluorination reaction the halogenation catalyst is antimony pentachloride and/or antimony pentafluoride, preferably wherein the catalyst is antimony pentafluoride ($SbF_5$) and is prepared in an autoclave by reaction of $SbCl_5$ with HF, more preferably consisting of $SbF_5$ in HF which forms the active species $H_2F^+SbF_6^-$, prior to a reaction step in the process according to any one of claims 1 to 17.

All reactions described can be carried out in the batch reactor or continuously in plug-flow or microreactors, using the microreactor example. Since SbV can be reduced partially to SbIII, optionally halogen in the form of chlorine or fluorine can be fed to any HF/catalyst recycle stream downstream of the phase separator (see WO03/053580). Moreover, since the mixture of highly fluorinated antimony (Sb) catalyst with excess HF is very corrosive, according to the invention, these reactions most preferably are carried out in SiC reactors or in HDPDFE coated reactors, or in reactors that lined accordingly with SiC or HDPDFE. Also some Al coatings have positive resistance.

If the end product is a solid, the purification is preferably carried out by recrystallization. If the product is a liquid or low-melting solid, it is purified by distillation, optionally by so-called solid distillation with heated condenser.

Further Details on the Reactors:

In the use and processes according to the invention in a preferred embodiment the invention is using a microreactor. But it is to be noted in a more general embodiment of the invention, apart from the said preferred embodiment of the invention that is using a microreactor, any other, e.g. preferentially pipe-like, continuous flow reactor with upper lateral dimensions of up to about 1 cm, and as defined herein, can be employed. Thus, such a continuous flow reactor preferably with upper lateral dimensions of up to about ≤5 mm, or of about ≤4 mm, refers to a preferred embodiment of the invention, e.g. preferably to a microreactor. Continuously operated series of STRs is another option, but less preferred than using a microreactor.

In the before said embodiments of the invention, the minimal lateral dimensions of the, e.g. preferentially pipe-like, continuous flow reactor can be about >5 mm; but is usually not exceeding about 1 cm. Thus, the lateral dimensions of the, e.g. preferentially pipe-like, continuous flow reactor can be in the range of from about >5 mm up to about 1 cm, and can be of any value therein between. For example, the lateral dimensions of the, e.g. preferentially pipe-like, continuous flow reactor can be about 5.1 mm, about 5.5 mm, about 6 mm, about 6.5 mm, about 7 mm, about 7.5 mm, about 8 mm, about 8.5 mm, about 9 mm, about 9.5 mm, and about 10 mm, or can be can be of any value intermediate between the said values.

In the before said embodiments of the invention using a microreactor preferentially the minimal lateral dimensions of the microreactor can be at least about 0.25 mm, and preferably at least about 0.5 mm; but the maximum lateral dimensions of the microreactor does not exceed about ≤5 mm. Thus, the lateral dimensions of the, e.g. preferential microreactor can be in the range of from about 0.25 mm up to about ≤5 mm, and preferably from about 0.5 mm up to about ≤5 mm, and can be of any value therein between. For example, the lateral dimensions of the preferential microreactor can be about 0.25 mm, about 0.3 mm, about 0.35 mm, about 0.4 mm, about 0.45 mm, and about 5 mm, or can be can be of any value intermediate between the said values.

As stated here before in the embodiments of the invention in its broadest meaning is employing, preferentially pipe-like, continuous flow reactor with upper lateral dimensions of up to about 1 cm. Such continuous flow reactor, for example is a plug flow reactor (PFR).

The plug flow reactor (PFR), sometimes called continuous tubular reactor, CTR, or piston flow reactors, is a reactor used to perform and describe chemical reactions in continuous, flowing systems of cylindrical geometry. The PFR reactor model is used to predict the behaviour of chemical reactors of such design, so that key reactor variables, such as the dimensions of the reactor, can be estimated.

Fluid going through a PFR may be modelled as flowing through the reactor as a series of infinitely thin coherent "plugs", each with a uniform composition, traveling in the axial direction of the reactor, with each plug having a different composition from the ones before and after it. The key assumption is that as a plug flows through a PFR, the fluid is perfectly mixed in the radial direction (i.e. in the lateral direction) but not in the axial direction (forwards or backwards).

Accordingly, the terms used herein to define the reactor type used in the context of the invention such like "continuous flow reactor", "plug flow reactor", "tubular reactor", "continuous flow reactor system", "plug flow reactor system", "tubular reactor system", "continuous flow system", "plug flow system", "tubular system" are synonymous to each other and interchangeably by each other.

The reactor or system may be arranged as a multitude of tubes, which may be, for example, linear, looped, meandering, circled, coiled, or combinations thereof. If coiled, for example, then the reactor or system is also called "coiled reactor" or "coiled system".

In the radial direction, i.e. in the lateral direction, such reactor or system may have an inner diameter or an inner cross-section dimension (i.e. radial dimension or lateral dimension, respectively) of up to about 1 cm. Thus, in an embodiment the lateral dimension of the reactor or system may be in the range of from about 0.25 mm up to about 1 cm, preferably of from about 0.5 mm up to about 1 cm, and more preferably of from about 1 mm up to about 1 cm.

In further embodiments the lateral dimension of the reactor or system may be in the range of from about >5 mm to about 1 cm, or of from about 5.1 mm to about 1 cm.

If the lateral dimension at maximum of up to about ≤5 mm, or of up to about ≤4 mm, then the reactor is called "microreactor". Thus, in still further microreactor embodiments the lateral dimension of the reactor or system may be in the range of from about 0.25 mm up to about ≤5 mm, preferably of from about 0.5 mm up to about ≤5 mm, and more preferably of from about 1 mm up to about ≤5 mm; or the lateral dimension of the reactor or system may be in the range of from about 0.25 mm up to about ≤4 mm, preferably of from about 0.5 mm up to about ≤4 mm, and more preferably of from about 1 mm up to about ≤4 mm.

In case reactants are solid inert solvents may be used. Thus, if raw materials shall be used, then the said solid raw materials are dissolved in an inert solvent. A suitable solvent is e.g. acetonitrile, or fully or partially fluorinated alkanes like Pentafluorobutane (365 mfc), linear or cyclic partially or fully fluorinated ethers like $CF_3$—$CH_2$—$OCHF_2$ (E245) or Octafluorotetrahydrofuran. Often, if available or after a first synthesis, the product as such can also serve as inert solvent.

In an alternative embodiment of the invention, it is also optionally desired to employ another continuous flow reactor than a microreactor, preferably if, for example, the (halogenation promoting, e.g. the halogenation or preferably the halogenation) catalyst composition used in the halogenation or fluorination tends to get viscous during reaction or is viscous already as a said catalyst as such. In such case, a continuous flow reactor, i.e. a device in which chemical reactions take place in a confinement with lower lateral dimensions of greater than that indicated above for a microreactor, i.e. of greater than about 1 mm, but wherein the upper lateral dimensions are about ≤4 mm. Accordingly, in this alternative embodiment of the invention, employing a continuous flow reactor, the term "continuous flow reactor" preferably denotes a device in which chemical reactions take place in a confinement with typical lateral dimensions of from about ≥1 mm up to about ≤4 mm. In such an embodiment of the invention it is particularly preferred to employ as a continuous flow reactor a plug flow reactor and/or a tubular flow reactor, with the said lateral dimensions. Also, in such an embodiment of the invention, as compared to the embodiment employing a microreactor, it is particularly preferred to employ higher flow rates in the continuous flow reactor, preferably in the plug flow reactor and/or a tubular flow reactor, with the said lateral dimensions. For example, such higher flow rates, are up to about 2 times higher, up to about 3 times higher, up to about 4 times higher, up to about 5 times higher, up to about 6 times higher, up to about 7 times higher, or any intermediate flow rate of from about ≥1 up to about ≤7 times higher, of from about ≥1 up to about ≤6 times higher, of from about ≥1 up to about ≤5 times higher, of from about ≥1 up to about ≤4 times higher, of from about ≥1 up to about ≤3 times higher, or of from about ≥1 up to about ≤2 times higher, each as compared to the typical flow rates indicated herein for a microreactor. Preferably, the said continuous flow reactor, more preferably the the plug flow reactor and/or a tubular flow reactor, employed in this embodiment of the invention is configured with the construction materials as defined herein for the microreactors. For example, such construction materials are silicon carbide (SiC) and/or are alloys such as a highly corrosion resistant nickel-chromium-molybdenum-tungsten alloy, e.g. Hastelloy®, as described herein for the microreactors.

A very particular advantage of the present invention employing a microreactor, or a continuous flow reactor with the before said lateral dimensions, the number of separating steps can be reduced and simplified, and may be devoid of time and energy consuming, e.g. intermediate, distillation steps. Especially, it is a particular advantage of the present invention employing a microreactor, or a continuous flow reactor with the before said lateral dimensions, that for separating simply phase separation methods can be employed, and the non-consumed reaction components may be recycled into the process, or otherwise be used as a product itself, as applicable or desired.

In addition to the preferred embodiments of the present invention using a microreactor according to the invention, in addition or alternatively to using a microreactor, it is also possible to employ a plug flow reactor or a tubular flow reactor, respectively.

Plug flow reactor or tubular flow reactor, respectively, and their operation conditions, are well known to those skilled in the field.

Although the use of a continuous flow reactor with upper lateral dimensions of about ≤5 mm, or of about ≤4 mm, respectively, and in particular of a microreactor, is particularly preferred in the present invention, depending on the circumstances, it could be imagined that somebody dispenses with an microreactor, then of course with yield losses and higher residence time, higher temperature, and instead takes a plug flow reactor or turbulent flow reactor, respectively. However, this could have a potential advantage, taking note of the mentioned possibly disadvantageous yield losses, namely the advantage that the probability of possible blockages (tar particle formation by non-ideal driving style) could be reduced because the diameters of the tubes or channels of a plug flow reactor are greater than those of a microreactor.

The possibly allegeable disadvantage of this variant using a plug flow reactor or a tubular flow reactor, however, may also be seen only as subjective point of view, but on the other hand under certain process constraints in a region or at a production facility may still be appropriate, and loss of yields be considered of less importance or even being acceptable in view of other advantages or avoidance of constraints.

In the following, the invention is more particularly described in the context of using a microreactor. Preferentially, a microreactor used according to the invention is a ceramic continuous flow reactor, more preferably anSiC (silicon carbide) continuous flow reactor, and can be used for material production at a multi-to scale. Within integrated heat exchangers and SiC materials of construction, it gives optimal control of challenging flow chemistry application. The compact, modular construction of the flow production reactor enables, advantageously for: long term flexibility towards different process types; access to a range of production volumes (5 to 400 l/h); intensified chemical production where space is limited; unrivalled chemical compatibility and thermal control.

Ceramic (SiC) microreactors, are e.g. advantageously diffusion bonded 3M SiC reactors, especially braze and metal free, provide for excellent heat and mass transfer, superior chemical compatibility, of FDA certified materials of construction, or of other drug regulatory authority (e.g. EMA) certified materials of construction. Silicon carbide (SiC), also known as carborundum, is a containing silicon and carbon, and is well known to those skilled in the art. For example, synthetic SiC powder is been mass-produced and processed for many technical applications.

For example, in the embodiments of the invention the objects are achieved by a method in which at least one reaction step takes place in a microreactor. Particularly, in preferred embodiments of the invention the objects are achieved by a method in which at least one reaction step takes place in a microreactor that is comprising or is made of SiC ("SiC-microreactor"), or in a microreactor that is comprising or is made of an alloy, e.g. such as Hastelloy C, as it is each defined herein after in more detail.

Thus, without being limited to, for example, in an embodiment of the invention the microreactor suitable for, preferably for industrial, production an "SiC-microreactor" that is comprising or is made of SiC (silicon carbide; e.g. SiC as offered by Dow Corning as Type GISiC or by Chemtrix MR555 Plantrix), e.g. providing a production capacity of from about 5 up to about 400 kg per hour; or without being limited to, for example, in another embodiment of the invention the microreactor suitable for industrial production is comprising or is made of Hastelloy C, as offered by Ehrfeld. Such microreactors are particularly suitable for the, preferably industrial, production of fluorinated products according to the invention.

In order to meet both the mechanical and chemical demands placed on production scale flow reactors, Plantrixmodules are fabricated from 3MmSiC (Grade C). Produced using the patented 3M (EP 1 637 271 B1 and foreign patents) diffusion bonding technology, the resulting monolithic reactors are hermetically sealed and are free from welding lines/joints and brazing agents. More technical information on the Chemtrix MR555 Plantrix can be found in the brochure "CHEMTRIX—Scalable Flow Chemistry—Technical Information Plantrix® MR555 Series, published by Chemtrix BV in 2017, which technical information is incorporated herein by reference in its entirety.

Apart from the before said example, in other embodiments of the invention, in general SiC from other manufactures, and as known to the skilled person, of course can be employed in the present invention.

Accordingly, in the present invention as microreactor also the Protrix® of by Chemtrix can be used. Protrix® is a modular, continuous flow reactor fabricated from 3M® silicon carbide, offering superior chemical resistance and heat transfer. In order to meet both the mechanical and chemical demands placed on flow reactors, Protrix® modules are fabricated from 3M® SiC (Grade C). Produced using the patented 3M (EP 1 637 271 Bi and foreign patents) diffusion bonding technology, the resulting monolithic reactors are hermetically sealed and are free from welding lines/joints and brazing agents. This fabrication technique is a production method that gives solid SiC reactors (thermal expansion coefficient=$4.1 \times 10^{-6} K^{-1}$).

Designed for flow rates ranging from 0.2 to 20 ml/minand pressures up to 25 bar, Protrix® allows the user to develop continuous flow processes at the lab-scale, later transitioning to Plantrix® MR555 (×340 scale factor) for material production. The Protrix® reactor is a unique flow reactor with the following advantages: diffusion bonded 3M® SiC modules with integrated heat exchangers that offer unrivaled thermal control and superior chemical resistance; safe employment of extreme reaction conditions on a g scale in a standard fumehood; efficient, flexible production in terms of number of reagent inputs, capacity or reaction time. The general specifications for the Protrix® flow reactors are summarized as follows; possible reaction types are, e.g. A+B→P1+Q (or C)→P, wherein the terms "A", "B" and "C" represent educts, "P" and "P1" products, and "Q" quencher; throughput (ml/min) of from about 0.2 up to about 20; channel dimensions (mm) of 1×1 (pre-heat and mixer zone), 1.4×1.4 (residence channel); reagent feeds of 1 to 3; module dimensions (width×height) (mm) of 110×260; frame dimensions (width×height×length) (mm) approximately 400×300× 250; number of modules/frame is one (minimum) up to four (max.). More technical information on the ChemtrixProtrix® reactor can be found in the brochure "CHEMTRIX—Scalable Flow Chemistry—Technical Information Protrix®, published by Chemtrix BV in 2017, which technical information is incorporated herein by reference in its entirety.

The Dow Corning as Type G1SiC microreactor, which is scalable for industrial production, and as well suitable for process development and small production can be characterized in terms of dimensions as follows: typical reactor size (length×width×height) of 88 cm×38 cm×72 cm; typical fluidic module size of 188 mm×162 mm. The features of the Dow Corning as Type G1SiC microreactor can be summarized as follows: outstanding mixing and heat exchange: patented HEART design; small internal volume; high residence time; highly flexible and multipurpose; high chemical durability which makes it suitable for high pH compounds and especially hydrofluoric acid; hybrid glass/SiC solution for construction material; seamless scale-up with other advanced-flow reactors. Typical specifications of the Dow Corning as Type GliSiC microreactor are as follows: flow rate of from about 30 ml/min up to about 200 ml/min; operating temperature in the range of from about −60° C. up to about 200° C., operating pressure up to about 18 barg ("barg" is a unit of gauge pressure, i.e. pressure in bars above ambient or atmospheric pressure); materials used are silicon carbide, PFA (perfluoroalkoxy alkanes), perfluoroelastomer; fluidic module of 10 ml internal volume; options: regulatory authority certifications, e.g. FDA or EMA, respectively. The reactor configuration of Dow Corning as Type GISiC microreactor is characterized as multipurpose and configuration can be customized. Injection points may be added anywhere on the said reactor.

Hastelloy® C is an alloy represented by the formula $NiCr_{21}Mo_{14}W$, alternatively also known as "alloy 22" or "Hastelloy® C-22. The said alloy is well known as a highly corrosion resistant nickel-chromium-molybdenum-tungsten alloy and has excellent resistance to oxidizing reducing and mixed acids. The said alloy is used in flue gas desulphurization plants, in the chemical industry, environmental protection systems, waste incineration plants, sewage plants. Apart from the before said example, in other embodiments of the invention, in general nickel-chromium-molybdenum-tungsten alloy from other manufactures, and as known to the skilled person, of course can be employed in the present invention. A typical chemical composition (all in weight-%) of such nickel-chromium-molybdenum-tungsten alloy is, each percentage based on the total alloy composition as 100%: Ni (nickel) as the main component (balance) of at least about 51.0%, e.g. in a range of from about 51.0% to about 63.0%; Cr (chromium) in a range of from about 20.0 to about 22.5%, Mo (molybdenum) in a range of from about 12.5 to about 14.5%, W (tungsten or wolfram, respectively) in a range of from about 2.5 to about 3.5%; and Fe (iron) in an amount of up to about 6.0%, e.g. in a range of from about 1.0% to about 6.0%, preferably in a range of from about 1.5% to about 6.0%, more preferably in a range of from about 2.0% to about 6.0%. Optionally, the percentage based on the total alloy composition as 100%, Co (cobalt) can be present in the alloy in an amount of up to about 2.5%, e.g. in a range of from about 0.1% to about 2.5%. Optionally, the percentage based on the total alloy composition as 100%, V (vanadium) can be present in the alloy in an amount of up to about 0.35%, e.g. in a range of from about 0.1% to about 0.35%. Also, the percentage based on the total alloy composition as 100%, optionally low amounts (i.e. ≤0.1%) of other element traces, e.g. independently of C (carbon), Si (silicon), Mn (manganese), P (phosphor), and/or S (sulfur). In such case of low amounts (i.e. ≤0.1%) of other elements, the said elements e.g. of C (carbon), Si (silicon), Mn (manganese), P (phosphor), and/or S (sulfur), the percentage based on the total alloy composition as 100%, each independently can be present in an amount of up to about 0.1%, e.g. each independently in a range of from about 0.01 to about 0.1%, preferably each independently in an amount of up to about 0.08%, e.g. each independently in a range of from about 0.01 to about 0.08%. For example, said elements e.g. of C (carbon), Si (silicon), Mn (manganese), P (phosphor), and/or S (sulfur), the percentage based on the total alloy composition as 100%, each independently can be present in an amount of, each value as an about value: C≤0.01%, Si≤0.08%, Mn≤0.05%, P≤0.015%, S≤0.02%.

Normally, no traceable amounts of any of the following elements are found in the alloy compositions indicated above: Nb (niobium), Ti (titanium), Al (aluminium), Cu (copper), N (nitrogen), and Ce (cerium).

Hastelloy® C-276 alloy was the first wrought, nickel-chromium-molybdenum material to alleviate concerns over welding (by virtue of extremely low carbon and silicon contents). As such, it was widely accepted in the chemical process and associated industries, and now has a 50-year-old track record of proven performance in a vast number of corrosive chemicals. Like other nickel alloys, it is ductile, easy to form and weld, and possesses exceptional resistance to stress corrosion cracking in chloride-bearing solutions (a form of degradation to which the austenitic stainless steels are prone). With its high chromium and molybdenum contents, it is able to withstand both oxidizing and non-oxidizing acids, and exhibits outstanding resistance to pitting and crevice attack in the presence of chlorides and other halides. The nominal composition in weight-% is, based on the total composition as 100%: Ni (nickel) 57% (balance); Co (cobalt) 2.5% (max.); Cr (chromium) 16%; Mo (molybdenum) 16%; Fe (iron) 5%; W (tungsten or wolfram, respectively) 4%; further components in lower amounts can be Mn (manganese) up to 1% (max.); V (vanadium) up to 0.35% (max.); Si (silicon) up to 0.08% (max.); C (carbon) 0.01 (max.); Cu (copper) up to 0.5% (max.).

In another embodiments of the invention, without being limited to, for example, the microreactor suitable for the said production, preferably for the said industrial production, is an SiC-microreactor that is comprising or is made only of SiC as the construction material (silicon carbide; e.g. SiC as offered by Dow Corning as Type GISiC or by Chemtrix MR555 Plantrix), e.g. providing a production capacity of from about 5 up to about 400 kg per hour.

It is of course possible according to the invention to use one or more microreactors, preferably one or more SiC-microreactors, in the production, preferably in the industrial production, of the fluorinated products according to the invention. If more than one microreactor, preferably more than one SiC-microreactors, are used in the production, preferably in the industrial production, of the fluorinated products according to the invention, then these microreactors, preferably these SiC-microreactors, can be used in parallel and/or subsequent arrangements. For example, two, three, four, or more microreactors, preferably two, three, four, or more SiC-microreactors, can be used in parallel and/or subsequent arrangements.

For laboratory search, e.g. on applicable reaction and/or upscaling conditions, without being limited to, for example, as a microreactor the reactor type Plantrix of the company Chemtrix is suitable. Sometimes, if gaskets of a microreactor are made out of other material than HDPTFE, leakage might occur quite soon after short time of operation because of some swelling, so HDPTFE gaskets secure long operating time of microreactor and involved other equipment parts like settler and distillation columns.

For example, an industrial flow reactor ("IFR", e.g. Plantrix® MR555) comprises of SiC modules (e.g. 3M® SiC) housed within a (non-wetted) stainless steel frame, through which connection of feed lines and service media are made using standard Swagelok fittings. The process fluids are heated or cooled within the modules using integrated heat exchangers, when used in conjunction with a service medium (thermal fluid or steam), and reacted in zig-zag or double zig-zag, meso-channel structures that are designed to give plug flow and have a high heat exchange capacity. A basic IFR (e.g. Plantrix® MR555) system comprises of one SiC module (e.g. 3M® SiC), a mixer ("MRX") that affords access to A+B→P type reactions. Increasing the number of modules leads to increased reaction times and/or system productivity. The addition of a quench Q/C module extends reaction types to A+B→P1+Q (or C)→P and a blanking plate gives two temperature zones. Herein the terms "A", "B" and "C" represent educts, "P" and "P1" products, and "Q" quencher.

Typical dimensions of an industrial flow reactor ("IFR", e.g. Plantrix® MR555) are, for example: channel dimensions in (mm) of 4×4 ("MRX", mixer) and 5×5 (MRH-I/MRH-II; "MR" denotes residence module); module dimensions (width×height) of 200 mm×555 mm; frame dimensions (width×height) of 322 mm×811 mm. A typical throughput of an industrial flow reactor ("IFR", e.g. Plantrix® MR555) is, for example, in the range of from about 50 l/h to about 400 l/h. in addition, depending on fluid properties and process conditions used, the throughput of an industrial flow reactor ("IFR", e.g. Plantrix® MR555), for example, can also be >400 l/h. The residence modules can be placed in series in order to deliver the required reaction volume or productivity. The number of modules that can be placed in series depends on the fluid properties and targeted flow rate.

Typical operating or process conditions of an industrial flow reactor ("IFR", e.g. Plantrix® MR555) are, for example: temperature range of from about −30° C. to about 200° C.; temperature difference (service−process)<70° C.; reagent feeds of 1 to 3; maximum operating pressure (service fluid) of about 5 bar at a temperature of about 200° C.; maximum operating pressure (process fluid) of about 25 bar at a temperature of about ≤200° C.

Further Details of the Reactors Used in the Invention:

As to the term "microreactor": A "microreactor" or "microstructured reactor" or "microchannel reactor", in one embodiment of the invention, is a device in which chemical reactions take place in a confinement with typical lateral dimensions of about ≤1 mm; an example of a typical form of such confinement are microchannels. Generally, in the context of the invention, the term "microreactor": A "microreactor" or "microstructured reactor" or "microchannel reactor", denotes a device in which chemical reactions take place in a confinement with typical lateral dimensions of about ≤5 mm, or of about ≤4 mm.

Microreactors are studied in the field of micro process engineering, together with other devices (such as micro heat exchangers) in which physical processes occur. The microreactor is usually a continuous flow reactor (contrast with/to a batch reactor). Microreactors offer many advantages over conventional scale reactors, including vast improvements in energy efficiency, reaction speed and yield, safety, reliability, scalability, on-site/on-demand production, and a much finer degree of process control.

Microreactors are used in "flow chemistry" to perform chemical reactions.

In flow chemistry, wherein often microreactors are used, a chemical reaction is run in a continuously flowing stream rather than in batch production. Batch production is a technique used in manufacturing, in which the object in question is created stage by stage over a series of workstations, and different batches of products are made. Together with job production (one-off production) and mass production (flow production or continuous production) it is one of the three main production methods. In contrast, in flow chemistry the chemical reaction is run in a continuously flowing stream, wherein pumps move fluid into a tube, and where tubes join one another, the fluids contact one another. If these fluids are reactive, a reaction takes place. Flow chemistry is a well-established technique for use at a large scale when manufacturing large quantities of a given material. However, the term has only been coined recently for its application on a laboratory scale.

Continuous flow reactors, e.g. such as used as microreactor, are typically tube like and manufactured from non-reactive materials, such known in the prior art and depending on the specific purpose and nature of possibly aggressive agents and/or reactants. Mixing methods include diffusion alone, e.g. if the diameter of the reactor is narrow, e.g. <1 mm, such as in microreactors, and static mixers. Continuous flow reactors allow good control over reaction conditions including heat transfer, time and mixing. The residence time of the reagents in the reactor, i.e. the amount of time that the reaction is heated or cooled, is calculated from the volume of the reactor and the flow rate through it: Residence time=Reactor Volume/Flow Rate. Therefore, to achieve a longer residence time, reagents can be pumped more slowly and/or a larger volume reactor used. Production rates can vary from milliliters minute to liters per hour.

Some examples of flow reactors are spinning disk reactors (Colin Ramshaw); spinning tube reactors; multi-cell flow reactors; oscillatory flow reactors; microreactors; hex reactors; and aspirator reactors. In an aspirator reactor a pump propels one reagent, which causes a reactant to be sucked in. Also to be mentioned are plug flow reactors and tubular flow reactors.

In the present invention, in one embodiment it is particularly preferred to employ a microreactor.

In an alternative embodiment of the invention, it is also optionally desired to employ another continuous flow reactor than a microreactor, preferably if, for example, the (halogenation promoting, e.g. the halogenation or preferably the halogenation) catalyst composition used in the halogenation or fluorination tends to get viscous during reaction or is viscous already as a said catalyst as such. In such case, a continuous flow reactor, i.e. a device in which chemical reactions take place in a confinement with lower lateral dimensions of greater than that indicated above for a microreactor, i.e. of greater than about 1 mm, but wherein the upper lateral dimensions are about ≤5 mm, or of about ≤4 mm. Accordingly, in this alternative embodiment of the invention, employing a continuous flow reactor, the term "continuous flow reactor" preferably denotes a device in which chemical reactions take place in a confinement with typical lateral dimensions of from about ≥1 mm up to about ≤5 mm, or of about ≤4 mm. In such an embodiment of the invention it is particularly preferred to employ as a continuous flow reactor a plug flow reactor and/or a tubular flow reactor, with the said lateral dimensions. Also, in such an embodiment of the invention, as compared to the embodiment employing a microreactor, it is particularly preferred to employ higher flow rates in the continuous flow reactor, preferably in the plug flow reactor and/or a tubular flow reactor, with the said lateral dimensions. For example, such higher flow rates, are up to about 2 times higher, up to about 3 times higher, up to about 4 times higher, up to about 5 times higher, up to about 6 times higher, up to about 7 times higher, or any intermediate flow rate of from about ≥1 up to about ≤7 times higher, of from about ≥1 up to about ≤6 times higher, of from about ≥1 up to about ≤5 times higher, of from about ≥1 up to about ≤4 times higher, of from about ≥1 up to about ≤3 times higher, or of from about ≥1 up to about ≤2 times higher, each as compared to the typical flow rates indicated herein for a microreactor. Preferably, the said continuous flow reactor, more preferably the the plug flow reactor and/or a tubular flow reactor, employed in this embodiment of the invention is configured with the construction materials as defined herein for the microreactors. For example, such construction materials are silicon carbide (SiC) and/or are alloys such as a highly corrosion resistant nickel-chromium-molybdenum-tungsten alloy, e.g. Hastelloy®, as described herein for the microreactors.

A very particular advantage of the present invention employing a microreactor, or a continuous flow reactor with the before said lateral dimensions, the number of separating steps can be reduced and simplified, and may be devoid of time and energy consuming, e.g. intermediate, distillation steps. Especially, it is a particular advantage of the present invention employing a microreactor, or a continuous flow reactor with the before said lateral dimensions, that for separating simply phase separation methods can be employed, and the non-consumed reaction components may be recycled into the process, or otherwise be used as a product itself, as applicable or desired.

Plug flow reactor or tubular flow reactor, respectively, and their operation conditions, are well known to those skilled in the field.

Although the use of a continuous flow reactor with upper lateral dimensions of about ≤5 mm, or of about ≤4 mm, and in particular of a microreactor, is particularly preferred in the present invention, depending on the circumstances, it could be imagined that somebody dispenses with an microreactor, then of course with yield losses and higher residence time, higher temperature, and instead takes a plug flow reactor or turbulent flow reactor, respectively. However, this could have a potential advantage, taking note of the mentioned possibly disadvantageous yield losses, namely the advantage that the probability of possible blockages (tar particle formation by non-ideal driving style) could be reduced because the diameters of the tubes or channels of a plug flow reactor are greater than those of a microreactor.

The possibly allegeable disadvantage of this variant using a plug flow reactor or a tubular flow reactor, however, may also be seen only as subjective point of view, but on the other hand under certain process constraints in a region or at a production facility may still be appropriate, and loss of yields be considered of less importance or even being acceptable in view of other advantages or avoidance of constraints.

In the following, the invention is more particularly described in the context of using a microreactor. Preferentially, a microreactor used according to the invention is a ceramic or high grade stainless steel (Inox or Hastelloy) continuous flow reactor, more preferably an SiC (silicon carbide) continuous flow reactor, and can be used for material production at a multi-to scale. Within integrated heat exchangers and SiC materials of construction, it gives optimal control of challenging flow chemistry application. The compact, modular construction of the flow production reactor enables, advantageously for: long term flexibility towards different process types; access to a range of production volumes (5 to 400 l/h); intensified chemical production where space is limited; unrivalled chemical compatibility and thermal control.

Ceramic (SiC) microreactors, are e.g. advantageously diffusion bonded 3M SiC reactors, especially braze and metal free, provide for excellent heat and mass transfer, superior chemical compatibility, of FDA certified materials of construction, or of other drug regulatory authority (e.g. EMA) certified materials of construction. Silicon carbide (SiC), also known as carborundum, is a containing silicon and carbon, and is well known to those skilled in the art. For example, synthetic SiC powder is been mass-produced and processed for many technical applications.

Thus, without being limited to, for example, in an embodiment of the invention the microreactor suitable for, preferably for industrial, production an "SiC-microreactor" that is comprising or is made of SiC (silicon carbide; e.g. SiC as offered by Dow Corning as Type GISiC or by Chemtrix MR555 Plantrix), e.g. providing a production capacity of from about 5 up to about 400 kg per hour; or without being limited to, for example, in another embodiment of the invention the microreactor suitable for industrial production is comprising or is made of Hastelloy C, as offered by Ehrfeld.

In order to meet both the mechanical and chemical demands placed on production scale flow reactors, Plantrixmodules are fabricated from 3MmSiC (Grade C). Produced using the patented 3M (EP 1 637 271 B1 and foreign patents) diffusion bonding technology, the resulting monolithic reactors are hermetically sealed and are free from welding lines/joints and brazing agents. More technical information on the Chemtrix MR555 Plantrix can be found in the brochure "CHEMTRIX—Scalable Flow Chemistry—Technical Information Plantrix® MR555 Series, published by Chemtrix BV in 2017, which technical information is incorporated herein by reference in its entirety.

Apart from the before said example, in other embodiments of the invention, in general SiC from other manufactures, and as known to the skilled person, of course can be employed in the present invention.

Accordingly, in the present invention as microreactor also the Protrix® of by Chemtrix can be used. Protrix® is a modular, continuous flow reactor fabricated from 3M® silicon carbide, offering superior chemical resistance and heat transfer. In order to meet both the mechanical and chemical demands placed on flow reactors, Protrix® modules are fabricated from 3M® SiC (Grade C).

Produced using the patented 3M (EP 1 637 271 Bi and foreign patents) diffusion bonding technology, the resulting monolithic reactors are hermetically sealed and are free from welding lines/joints and brazing agents. This fabrication technique is a production method that gives solid SiC reactors (thermal expansion coefficient=$4.1\times10^{-6}K^{-1}$).

Designed for flow rates ranging from 0.2 to 20 ml/min and pressures up to 25 bar, Protrix® allows the user to develop continuous flow processes at the lab-scale, later transitioning to Plantrix® MR555 (×340 scale factor) for material production. The Protrix® reactor is a unique flow reactor with the following advantages: diffusion bonded 3M® SiCmodules with integrated heat exchangers that offer unrivaled thermal control and superior chemical resistance; safe employment of extreme reaction conditions on a g scale in a standard fumehood; efficient, flexible production in terms of number of reagent inputs, capacity or reaction time. The general specifications for the Protrix® flow reactors are summarized as follows; possible reaction types are, e.g. A+B→P1+Q (or C)→P, wherein the terms "A", "B" and "C" represent educts, "P" and "P1" products, and "Q" quencher; throughput (ml/min) of from about 0.2 up to about 20; channel dimensions (mm) of 1×1 (pre-heat and mixer zone), 1.4×1.4 (residence channel); reagent feeds of 1 to 3; module dimensions (width×height) (mm) of 110×260; frame dimensions (width×height×length) (mm) approximately 400×300×250; number of modules/frame is one (minimum) up to four (max.). More technical information on the ChemtrixProtrix® reactor can be found in the brochure "CHEMTRIX—Scalable Flow Chemistry—Technical Information Protrix®, published by Chemtrix BV in 2017, which technical information is incorporated herein by reference in its entirety.

The Dow Corning as Type G1SiC microreactor, which is scalable for industrial production, and as well suitable for process development and small production can be characterized in terms of dimensions as follows: typical reactor size (length×width×height) of 88 cm×38 cm×72 cm; typical fluidic module size of 188 mm×162 mm. The features of the Dow Corning as Type G1SiC microreactor can be summarized as follows: outstanding mixing and heat exchange: patented HEART design; small internal volume; high residence time; highly flexible and multipurpose; high chemical durability which makes it suitable for high pH compounds and especially hydrofluoric acid; hybrid glass/SiC solution for construction material; seamless scale-up with other advanced-flow reactors. Typical specifications of the Dow Corning as Type G1SiC microreactor are as follows: flow rate of from about 30 ml/min up to about 200 ml/min; operating temperature in the range of from about −60° C. up to about 200° C., operating pressure up to about 18 barg ("barg" is a unit of gauge pressure, i.e. pressure in bars above ambient or atmospheric pressure); materials used are silicon carbide, PFA (perfluoroalkoxy alkanes), perfluoroelastomer; fluidic module of 10 ml internal volume; options: regulatory authority certifications, e.g. FDA or EMA, respectively. The reactor configuration of Dow Corning as Type GISiC microreactor is characterized as multipurpose and configuration can be customized. Injection points may be added anywhere on the said reactor.

Hastelloy® C is an alloy represented by the formula NiCr21Mol4W, alternatively also known as "alloy 22" or "Hastelloy® C-22. The said alloy is well known as a highly corrosion resistant nickel-chromium-molybdenum-tungsten alloy and has excellent resistance to oxidizing reducing and mixed acids. The said alloy is used in flue gas desulphurization plants, in the chemical industry, environmental protection systems, waste incineration plants, sewage plants. Apart from the before said example, in other embodiments of the invention, in general nickel-chromium-molybdenum-tungsten alloy from other manufactures, and as known to the skilled person, of course can be employed in the present invention. A typical chemical composition (all in weight-%) of such nickel-chromium-molybdenum-tungsten alloy is, each percentage based on the total alloy composition as 100%: Ni (nickel) as the main component (balance) of at least about 51.0%, e.g. in a range of from about 51.0% to about 63.0%; Cr (chromium) in a range of from about 20.0 to about 22.5%, Mo (molybdenum) in a range of from about 12.5 to about 14.5%, W (tungsten or wolfram, respectively) in a range of from about 2.5 to about 3.5%; and Fe (iron) in an amount of up to about 6.0%, e.g. in a range of from about 1.0% to about 6.0%, preferably in a range of from about 1.5% to about 6.0%, more preferably in a range of from about 2.0% to about 6.0%. Optionally, the percentage based on the total alloy composition as 100%, Co (cobalt) can be present in the alloy in an amount of up to about 2.5%, e.g. in a range of from about 0.1% to about 2.5%. Optionally, the percentage based on the total alloy composition as 100%, V (vanadium) can be present in the alloy in an amount of up to about 0.35%, e.g. in a range of from about 0.1% to about 0.35%. Also, the percentage based on the total alloy composition as 100%, optionally low amounts (i.e. ≤0.1%) of other element traces, e.g. independently of C (carbon), Si (silicon), Mn (manganese), P (phosphor), and/or S (sulfur). In such case of low amounts (i.e. ≤0.1%) of other elements, the said elements e.g. of C (carbon), Si (silicon), Mn (manganese), P (phosphor), and/or S (sulfur), the percentage based on the total alloy composition as 100%, each independently can be present in an amount of up to about 0.1%, e.g. each independently in a range of from about 0.01 to about 0.1%, preferably each independently in an amount of up to about 0.08%, e.g. each independently in a range of from about 0.01 to about 0.08%. For example, said elements e.g. of C (carbon), Si (silicon), Mn (manganese), P (phosphor), and/or S (sulfur), the percentage based on the total alloy composition as 100%, each independently can be present in an amount of, each value as an about value: C≤0.01%, Si≤0.08%, Mn≤0.05%, P≤0.015%, S≤0.02%. Normally, no traceable amounts of any of the following elements are found in the alloy compositions indicated above: Nb (niobium), Ti (titanium), Al (aluminium), Cu (copper), N (nitrogen), and Ce (cerium).

Hastelloy® C-276 alloy was the first wrought, nickel-chromium-molybdenum material to alleviate concerns over welding (by virtue of extremely low carbon and silicon contents). As such, it was widely accepted in the chemical process and associated industries, and now has a 50-year-old track record of proven performance in a vast number of corrosive chemicals. Like other nickel alloys, it is ductile, easy to form and weld, and possesses exceptional resistance to stress corrosion cracking in chloride-bearing solutions (a form of degradation to which the austenitic stainless steels are prone). With its high chromium and molybdenum contents, it is able to withstand both oxidizing and non-oxidizing acids, and exhibits outstanding resistance to pitting and crevice attack in the presence of chlorides and other halides. The nominal composition in weight-% is, based on the total composition as 100%: Ni (nickel) 57% (balance); Co (cobalt) 2.5% (max.); Cr (chromium) 16%; Mo (molybdenum) 16%; Fe (iron) 5%; W (tungsten or wolfram, respectively) 4%; further components in lower amounts can be Mn (manganese) up to 1% (max.); V (vanadium) up to 0.35% (max.); Si (silicon) up to 0.08% (max.); C (carbon) 0.01 (max.); Cu (copper) up to 0.5% (max.).

In another embodiments of the invention, without being limited to, for example, the microreactor suitable for the said production, preferably for the said industrial production, is an SiC-microreactor that is comprising or is made only of SiC as the construction material (silicon carbide; e.g. SiC as offered by Dow Corning as Type G1SiC or by Chemtrix MR555 Plantrix), e.g. providing a production capacity of from about 5 up to about 400 kg per hour.

It is of course possible according to the invention to use one or more microreactors, preferably one or more SiC-microreactors, in the production, preferably in the industrial production, of the targeted compounds described herein in the context of the invention. If more than one microreactor, preferably more than one SiC-microreactors, are used in the production, preferably in the industrial production, then these microreactors, preferably these SiC-microreactors, can be used in parallel and/or subsequent arrangements. For example, two, three, four, or more microreactors, preferably two, three, four, or more SiC-microreactors, can be used in parallel and/or subsequent arrangements.

For laboratory search, e.g. on applicable reaction and/or upscaling conditions, without being limited to, for example, as a microreactor the reactor type Plantrix of the company Chemtrix is suitable.

For example, an industrial flow reactor ("IFR", e.g. Plantrix® MR555) comprises of SiC modules (e.g. 3M® SiC) housed within a (non-wetted) stainless steel frame, through which connection of feed lines and service media are made using standard Swagelok fittings. The process fluids are heated or cooled within the modules using integrated heat exchangers, when used in conjunction with a service medium (thermal fluid or steam), and reacted in zig-zag or double zig-zag, meso-channel structures that are designed to give plug flow and have a high heat exchange capacity. A basic IFR (e.g. Plantrix® MR555) system comprises of one SiC module (e.g. 3M® SiC), a mixer ("MRX") that affords access to A+B→P type reactions. Increasing the number of modules leads to increased reaction times and/or system productivity. The addition of a quench Q/C module extends reaction types to A+B→P1+Q (or C)→P and a blanking plate gives two temperature zones. Herein the terms "A", "B" and "C" represent educts, "P" and "P1" products, and "Q" quencher.

Typical dimensions of an industrial flow reactor ("IFR", e.g. Plantrix® MR555) are, for example: channel dimensions in (mm) of 4×4 ("MRX", mixer) and 5×5 (MRH-I/MRH-II; "MR" denotes residence module); module dimensions (width×height) of 200 mm×555 mm; frame dimensions (width×height) of 322 mm×811 mm. A typical throughput of an industrial flow reactor ("IFR", e.g. Plantrix® MR555) is, for example, in the range of from about 50 l/h to about 400 l/h. in addition, depending on fluid properties and process conditions used, the throughput of an industrial flow reactor ("IFR", e.g. Plantrix® MR555), for example, can also be ≥400 l/h. The residence modules can be placed in series in order to deliver the required reaction volume or productivity. The number of modules that can be placed in series depends on the fluid properties and targeted flow rate.

Typical operating or process conditions of an industrial flow reactor ("IFR", e.g. Plantrix® MR555) are, for example: temperature range of from about −30° C. to about 200° C.; temperature difference (service−process)<70° C.;

reagent feeds of 1 to 3; maximum operating pressure (service fluid) of about 5 bar at a temperature of about 200° C.; maximum operating pressure (process fluid) of about 25 bar at a temperature of about ≤200° C.

The following examples are intended to further illustrate the invention without limiting its scope.

EXAMPLES

Example 1

The synthesis flow in microreactors for 4,4'-dichlorobenzophenone, and the reaction scheme and the conditions are given below.

4-Chlorobenzoylchloride is pre-mixed with the HF+catalyst mixture, preferably in a mixing system (e.g., a split and recombine system) to form at least partially chlorobenzoylfluoride and the corresponding SbHal6-complex which meets the chlorobenzene before the mixture enters microreactor 1 (material of construction is SiC).

The reaction is performed as a Friedel-Crafts reaction.
Chemistry in (Microreactor, Friedel-Crafts Acylation:

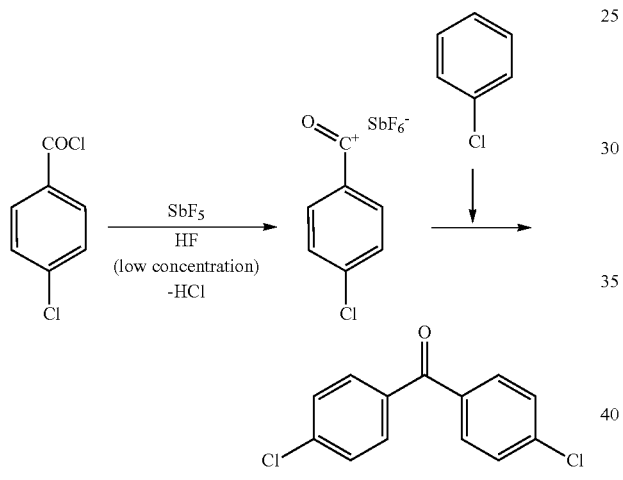

If a settler of sufficient size is used, the HF-catalyst mixture will separate from organic material which mainly is the 4,4'-dichlorobenzophenone. In the next step the HF/catalyst mixture needs to be converted into a nucleophilic fluorinating agent by adding an excess of HF vs. the Sb molar ratio which should be greater than 10 (HF:Sb=>10:1) before it enters microreactor 2. The reaction is also possible without a settler after microreactor I and without phase separation, but process control in industrial scale might be easier with that concept and a settler after microreactor 1.

The Friedel-Crafts reaction may be followed by a fluorination step, if desired, for converting the 4,4'-dichlorobenzophenone into 4,4'-difluorobenzophenone.

Example 2

The CCl4-route according to the invention, and the reaction scheme is given below, The reaction conditions are as given in Example 1.

In this example according to $CCl_4$-route, a Friedel-Crafts reaction with $CCl_4$, like illustrated in the scheme below, fluorobenzene is used as starting material, which may have been obtained by a fluorination of chlorobenzene prior to the Friedel-Crafts reaction:

Chemistry in (Microreactor), Friedel-Crafts Acylation:

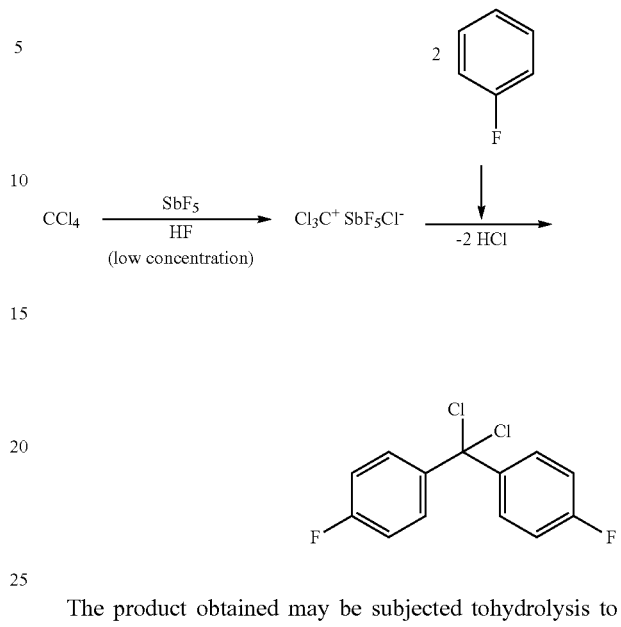

The product obtained may be subjected to hydrolysis to form a 4,4'-difluorobenophenone compound.

Example 3

The 4-chlorobenzylchlorid route according to the invention, and the reaction scheme is given below. The reaction conditions are as given in Example 1.

Chemistry (Microreactor), Friedel-Crafts Acylation:

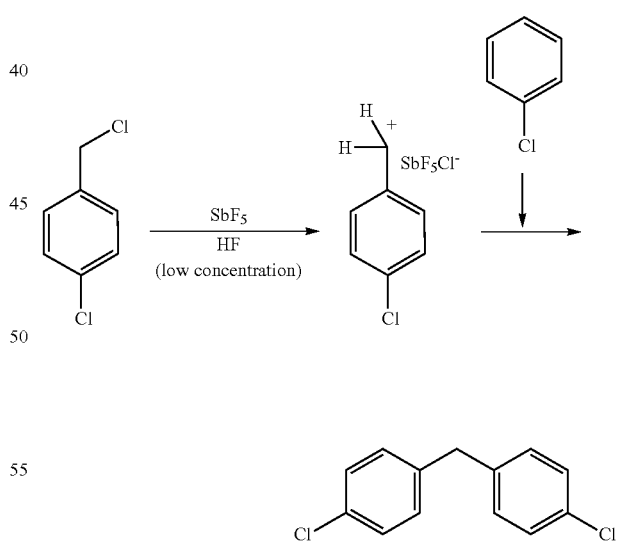

The product obtained may be subjected to a fluorination process to form a difluorodiphenylmethane compound.

Example 4

Friedel-Crafts alkylation and acylation in agro- and pharma applications.

This example relates to anti-HIV Efavirenz (Sustiva):

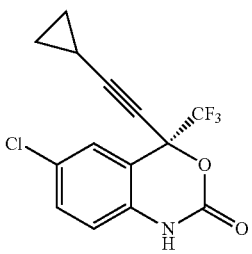 [SMILES: O=C1Nc2ccc(Cl)cc2[C@](C#CC2CC2)(C(F)(F)F)O1]

Efavirenz (Sustiva), described e.g. in EP582455 (1994) and U.S. Pat. No. 5,633,405 (1997) contain the trifluoroacetyl group containing intermediate which is made by Friedel Crafts. E.g. described in a newer publication by Chu, Haiyan in Faming ZhuanliShenging (2015), CN 104744392 A Jul. 1, 2015, the key precursor, the 4-chloro-2-trifluoracetyl aniline is made by expensive and challenging and expensive deep temperature chemistry using BuLi(butyl lithium) and ethyl trifluoro acetate as $CF_3$-group donor. The NH2-group has to be covered by a protecting group before, the protecting group has to be removed afterwards.

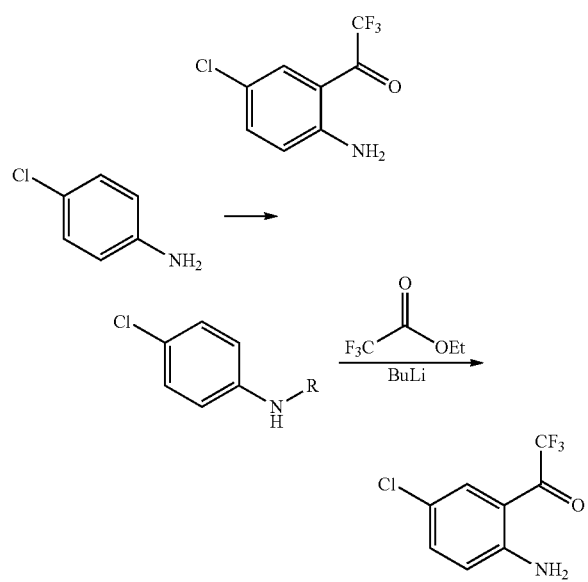

R = protecting group.

By Golubev, A. S. et al in Russian Chemical Bulletin, 63(10), 2264-2270; 2014, the trifluoroacylation is made with dichlorobenzene as starting material followed by introduction of the anline-$NH_2$ with azide chemistry afterwards. Other multistep synthesis routes from 4-Chloroaniline are described by Zhu, Lingjian et al inEuropean Journal of Medicinal Chemistry, 45(7), 2726-2732; 2010, and e.g., also with expensive $CF_3$-TMS as $CF_3$-group donor by Allendoerfer, Nadine et al from Tetrahedron Letters, 53(4), 388-391; 2012. But $CF_3$-TMS is very expensive and NOT available in larger industrial scale needed for Efavirenz.

Using the Sb system is suitable for benzene as such as a trifluoroacetyl group is deactivating the aromatic system and directs the formation of a Chlorobenzene derivative which is made by known methods (e.g. $FeCl_3+Cl_2$) to the meta position. The needed aniline derivative can be made e.g. by Nitration/$H_2$-reduction afterwards. Trifluoroacetylchloride is the direct next compound of photooxidation of HCFC-123 to TFAC and available in large industrial scale, whereas $CF_3$-TMS and some others are not. Ethyl trifluoroacetate is industrial available, Trifluoroacetic acid anhydride also could be used as $CF_3$-group donor, but is less favourable as they are more expensive and only parts of the molecule are used (worse atom efficiency).

Batch Example

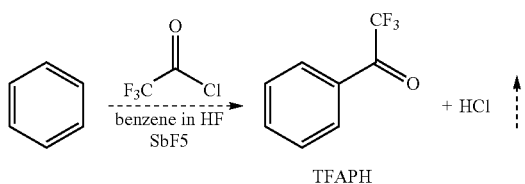

TFAPH

To 100 g (1.28 mol) benzene in a 250 ml Roth autoclave containing 21.68 g (0.1 mol) $SbF_5$ in 20 g (1.0 mol) HF as solvent is added 132.47 g (1.0 mol) trifluoroacetylchloride (TFAC) at room temperature out of the liquid phase of a stainless steel cylinder pressurized with $N_2$. The mixture is heated to 80° C. for 2 h, the pressure has started to increase immediately after adding TFAC probably by (at least some formation) of free HCl by trifluoroacetylchoride reaction with HF to trifluoroacetylfluoride (TFAC+HF→TFAF+ HCl). The autoclave was cooled down and just for easiness hydrolyzed in water. The yield in trifluoroacetophenone (TFAPH) after neutralisation, phase separation and distillation at reduced pressure (boiling point: 53° C., 20 mbar) was 150 g (86% of theory).

Continuous Example

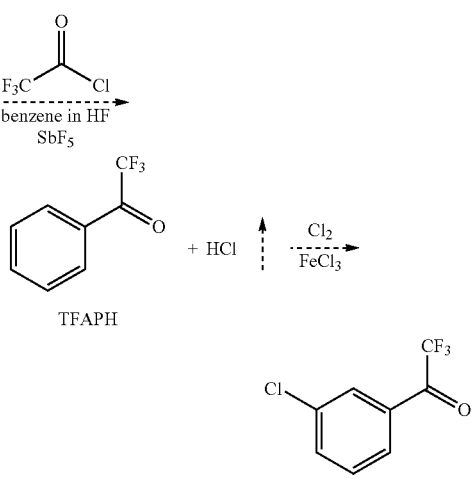

TFAPH

The reaction flow scheme is shown in FIG. 1 (reaction involving a microreactor).

The needed $FeCl_3$ for the chlorination reaction is added into the pure TFAPH after the distillation. The crude 3-chloro-trifluoroacetphenone finally is purified continuously in a stainless steel column.

Example 5

Industrial example of Friedel-Crafts alkylation.

STATE OF THE ART

Benzotrifluorides are usually made by chlorination of the corresponding $CH_3$-compounds followed by fluorination with anhydrous HF. This reaction procedure is industrial feasible, gives high yields and produces just HCl which even can be sold after further purification. For this type of reaction a Friedel-Crafts would not provide any advantage but could be applied e.g. $CF_3I$ or $CF_3Br$ and $CF_3Cl$, just in case. The situation is very different e.g. for perfluoroalkylated benzene derivatives like the heptafluorisopropyl methyl aniline needed for the agrochemical active ingredients like e.g. Flubendiamide (EP0919542 (1999)) and Pyrifluquinazon (EP1626047 (2006)).

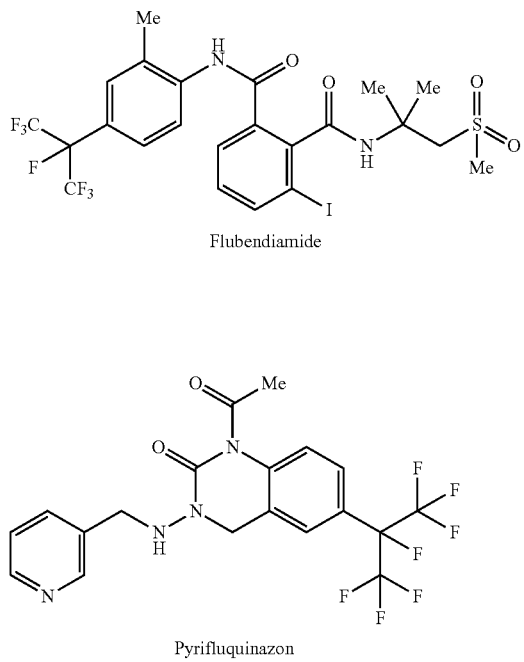

Flubendiamide

Pyrifluquinazon

For both intermediates, the heptafluoroisopropyl methyl aniline is necessary. It is prepared according to U.S. Pat. No. 6,600,074 (2002) and EP1380568 (2004) by a Friedel-Crafts reaction using $Na_2S_2O_4$ and heptafluoroisopropyliodide as starting materials.

This is a typical electrophilic reaction (as methylaniline is substituted by electron donating/pushing substituents). Draw back in industrial scale is the need of expensive heptafluoroisopropyliodide, and the need of recycling of the Iodine out of the waste is a must but, if possible either, very expensive. Iodine per se is an expensive leaving group and the formation of waste which is contaminated with toxic fluorinated compounds and Na-salts is another big drawback of said reaction even if the described yields are quite good.

Prior Art Reaction at Present

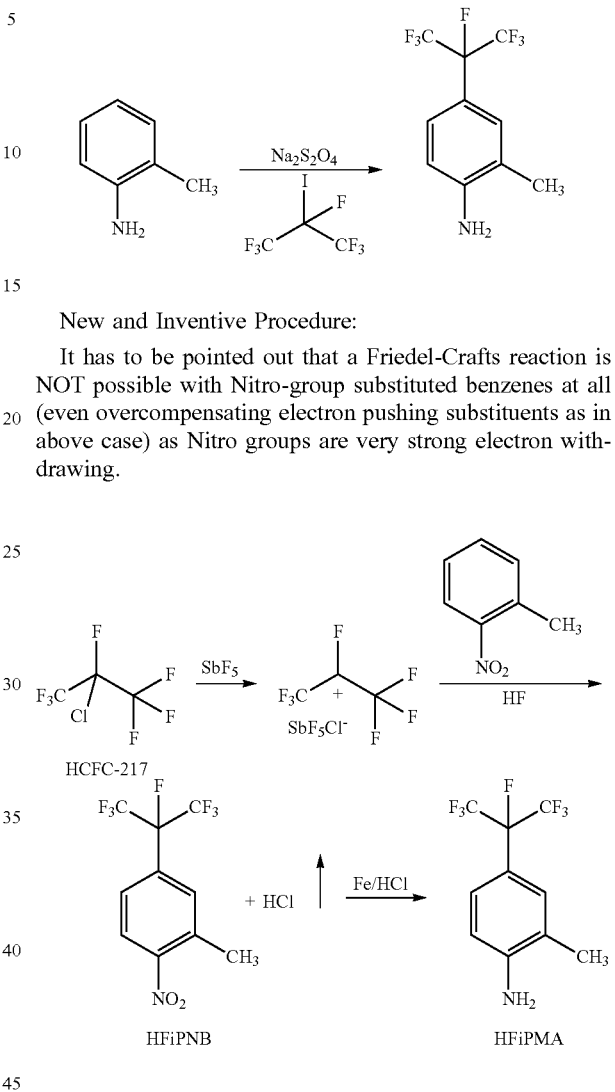

New and Inventive Procedure:

It has to be pointed out that a Friedel-Crafts reaction is NOT possible with Nitro-group substituted benzenes at all (even overcompensating electron pushing substituents as in above case) as Nitro groups are very strong electron withdrawing.

HCFC-217

HFiPNB      HFiPMA

Using a Sb catalyst also allows the usage of the corresponding heptafluoroisopropyl chloride which—with chlorine—contain a very common and cheap leaving group. Mechanistically, in a first step the reactive heptafluoroisopropylation/Sb complex is formed which undergoes reaction with the electron deficient nitrobenzene to give the heptafluoroisopropyl benzene derivative heptafluoroisopropyl-3-methyl-4-nitrobenzene (HFiPNB) and liberates just HCl as side product. As the heptafluoroisopropyl-4-nitro-3-methylbenzene (HFiPNB) is very stable, the continuing reduction of the $NO_2$-group to the amino group to form the needed HFiPMA is a quite reasonable step. (Unfortunately Sb catalyst for Friedel-Crafts cannot be applied for unprotected $NH_2$-groups in the starting materials, but this belongs to other than the inventive considered procedure). The Friedel-Crafts product HFiPNB is also an intermediate in newly described agricultural and horticultural insecticides (example 12 in US 2001/0041814), but there it is made out of expensive iodo-nitrotoluene which might not be industrial feasible and which has the same drawbacks with the iodine as already mentioned.

Procedure:

Example 5A and 5B, Synthesis of HCFC-217

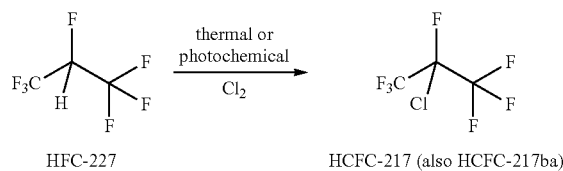 [SMILES: FC(C(F)(F)F)C(F)(F)F ; "Cl2" ; FC(F)(F)C(F)(Cl)C(F)(F)F]

HFC-227 → HCFC-217 (also HCFC-217ba)

Heptafluoroisopropylchloride ($(CF_3)_2CFCl$=HCFC-217) is prepared by thermal chlorination (example 1) of heptafluoropropane (HFC-227). HFC-227 is a product available in large industrial scale and used as a fire extinguishing agent (the thermal chlorination procedure is disclosed (but without purification) by Iikubo, Yuichi; Hedrick, Vicki; Brandstadter, Stephen M.; Cohn, Mitchel in U.S. Pat. Appl. Publ. (2004), US 20040127757). This procedure's focus is not the synthesis of HFC-217 but the recycling of CFC intermediates to valuable products. In a comparative trial according to this thermal procedure, the isolated yield was only 54%.

Another here applied procedure (example 2) is the photochlorination of HFC-227 using a TQ 718 Hg-lamp by passing an equimolar stream (per hour) of 400 g (2.35 mol) HFC-227 and $Cl_2$ in the gas phase at 50° C. over gas flow meters (Rotameter) continuously through a photoreactor made out of Duran 50 glass with 3 l gas volume. In both procedures (example1+2) the HCFC-217 was collected in a dry ice/MeOH cooling trap and purified afterwards by distillation in a pressurized stainless steel column. In the described photochemical procedure, the isolated yield collected in a stainless steel cylinder during distillation, was 98% (of theory).

Example 5C, Batch: (Inventive)

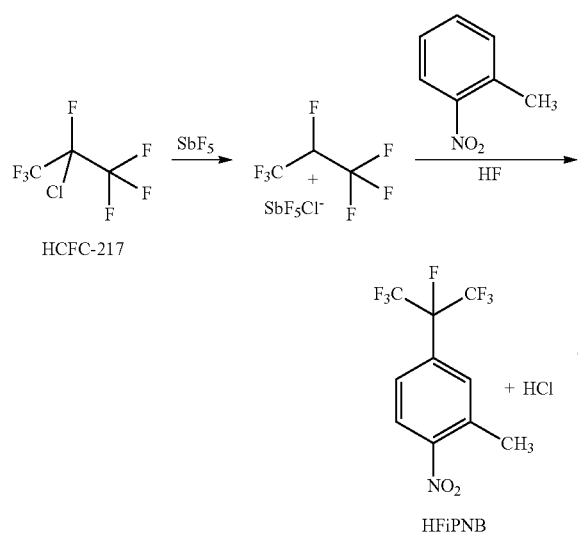

In a 250 ml Roth autoclave, 67.2 g (0.49 mol) 2-nitrotoluene containing 10.84 g (0.05 mol) $SbF_5$ in 1 g (0.05 mol) HF as solvent 100 g (0.49 mol) HCFC-217 is added out of a pressure cylinder. The mixture is heated to 80° C. for 2 h, the pressure has started to increase already while heating up. After the 2 h the autoclave was cooled down and the content was hydrolyzed in water the organic phase separated, dried with $Na_2SO_4$ and distilled. The yield in Heptafluoroisopropyl-3-methyl-4-nitrobenzol (HFiPNB) was 145 g, 97% (of theory).

Example 5D, Batch (not Inventive)

Recipe was repeated according to US 2001/0041814, example 12-2.

11.4 g (0.0374 mol) of 2-methyl-4-(heptafluoropropan-2-yl)-nitrobenzene in 60 ml Ethanol, and a solution of 29.5 g of $SnCl_2.2H_2O$ in 40 ml of hydrochloric acid was added dropwise thereto under ice-cooling over a period of 30 minutes. After completion of the dropwise addition, the reaction was carried out at room temperature for 2 hours. After completion of the reaction, the reaction solution was poured into 200 ml of ice water and neutralized with a 40% aqueous sodium hydroxide solution under ice-cooling. Then, a 40% aqueous sodium hydroxide solution was further added thereto until a homogeneous solution was obtained, and the desired compound was extracted with 100 ml of ether. The extract solution was washed with water, dried over anhydrous sodium sulfate and then concentrated, after which the residue was purified by vacuum distillation to obtain 9.8 g of the desired compound which corresponds to 84% (of theory).

Example 5E, Batch, Inventive

The reduction with Fe/HCl was done according to the procedure described by Fox, B. A.; Threlfall, T. L. (1973) for 2,3-iamonopyridine in Organic Syntheses.; Collective Volume, 5, p. 346.

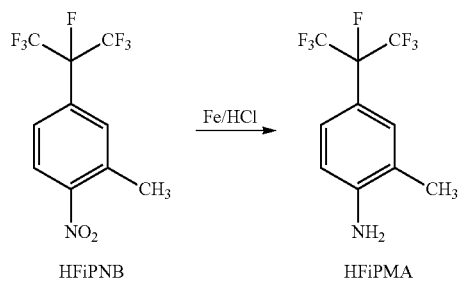 [SMILES: Cc1cc(C(F)(C(F)(F)F)C(F)(F)F)ccc1[N+](=O)[O-] ; "Fe/HCl" ; Cc1cc(C(F)(C(F)(F)F)C(F)(F)F)ccc1N]

HFiPNB → HFiPMA

A 100-ml. flask fitted with a reflux condenser is charged with 15.26 g. (0.05 mole) of HFiPNB, 30 g of reduced iron, 40 ml. of 95% ethanol, 10 ml. of water, and 0.5 ml. of concentrated hydrochloric acid. The mixture is heated on a steam bath for 1 hour, and at the end of this period the iron is removed by filtration and is washed three times with 10-ml. portions of hot 95% ethanol. The filtrate and washings are evaporated to dryness, and the dark residue is recrystallized from 50 ml. of water, 1 g of activated carbon being used and the mixture being filtered while hot. The charcoal is washed with hot ethanol to avoid losses. The obtained HFiPMA yield was 94% (13.8 g) after final distillation at reduced pressure (boiling point: 118° C., 20 mbar).

Example 5F, Continuous Procedure in 1 Microreactors and 2 Semi Batch Reactors (Inventive)

The reaction flow scheme for the production of heptafluoro-3-methyl nitorbenzen is shown in FIG. 2.

Remark: reduction step was kept as semi batch due to the possibility of blocking of microreactor channels by the Fe particles but in principle a replacement of the 2 batch reactors by microreactor could be possible also when challenging.

In continuous/semi-continuous manufacture the raw materials were fed into a 1st 27 ml Chemtrixmicroreactor made out of SiC at 60° C. 500 g (3.6 mol) 2-methylnitrobenzene and 260 g (1.2 mol) $SbF_5$) dissolved in 12.06 g (0.6 mol) HF (as solvent) were fed per hour together with 736.1 g (3.6 mol) HCFC-217 into microreactor 1. The HCl were let escape over a cyclone. The present HF and $SbF_5$ separates in a settler into a 2nd phase. The HFiPNB phase was subjected to a continuous operated fine distillation and isolated at boiling point 135° C., 20 mbar. This material is converted to HFiPMA with a very economic procedure by using Fe/HCl in Ethanol as described already in example 5E. The yield over the 2 steps was 94% in HFiPMA.

What is claimed is:

1. A process of preparing a compound by Friedel-Crafts reaction from a starting material compound, characterized in that the reaction is performed in the presence of an activated antimony pentahalide catalyst ($SbHal_5$) and activated by hydrogen fluoride (HF);
   wherein the process of preparing the compound by Friedel-Crafts reaction is a continuous process and the continuous process is performed in at least one SiC-microreactor, and the starting material compound is fluorinated in a fluorination reaction prior to the Friedel-Crafts reaction, or the compound prepared by Friedel-Crafts reaction from said starting material compound is fluorinated in a fluorination reaction after the Friedel-Crafts reaction;
   wherein the starting material compound is a compound of the formula (I):

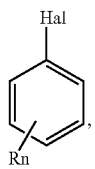
   (I)

wherein in the formula (I),
   Rn independently denotes one or more substituents selected from the group consisting of hydrogen (H), nitrogendioxide ($NO_2$), halogen, a substituted or unsubstituted $C_1$-$C_4$ alkyl, a substituted or unsubstituted C1-C4 alkoxy, a substituted or unsubstituted $C_1$-$C_4$ haloalkyl wherein the halogen is selected from the group consisting of fluorine (F), chlorine (Cl), bromine (Br) and Iodine (I), and a substituted or unsubstituted $C_1$-$C_4$ haloalkoxy wherein the halogen is selected from the group consisting of fluorine (F), chlorine (Cl), bromine (Br) and Iodine (I); and
   Hal denotes a halogen having chloro group:
   wherein the fluorination reaction is a continuous process and is performed in at least one SiC-microreactor under the following conditions:
   flow rate: of from about 10 ml/h up to about 400 l/h;
   temperature: of from about 30° C. up to about 150° C.;
   pressure: of from about 4 bar up to about 50 bar; and
   residence time: of from about 1 second up to about 60 minutes;
   wherein a Friedel-Crafts reagent is selected from the group consisting of the compounds having the formula (II), the formula (III), and the formula (IV):

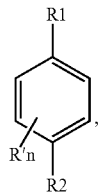
   (II)

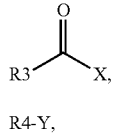
   (III)

R4-Y,
   (IV)

wherein in the formula (II):
   R'n independently denotes one or more substituents selected from the group consisting of hydrogen (H), nitrogen dioxide ($NO_2$), halogen, a substituted or unsubstituted $C_1$-$C_4$ alkyl, a substituted or unsubstituted $C_1$-$C_4$ alkoxy, a substituted or unsubstituted $C_1$-$C_4$ haloalkyl wherein the halogen is selected from the group consisting of fluorine (F), chlorine (Cl), bromine (Br) and Iodine (I), and a substituted or unsubstituted $C_1$-$C_4$ haloalkoxy group wherein the halogen (Hal) is selected from the group consisting of fluorine (F), chlorine (Cl), bromine (Br) and Iodine (I); and
   R1 and R2 independently from each other denote a hydrogen, a tri-halogeno methyl group (—$CHal_3$), a halogenocarbonyl group (—(C=O)Hal) or a halogeno methyl group (—$CH_2Hal$), and at least one of R1 and R2 is a tri-halogeno methyl group (—$CHal_3$), and a halogeno carbonyl group (—(C=O)Hal) or a halogeno methyl group (—$CH_2Hal$), wherein each halogen (Hal) is selected from the group consisting of fluorine (F), chlorine (Cl), bromine (Br) and Iodine (I);
   wherein in the formula (III):
   R3 independently denotes a substituted or unsubstituted $C_1$-$C_4$ alkyl, a substituted or unsubstituted C1-C4 haloalkyl wherein the halogen is selected from the group consisting of fluorine (F) and chlorine, and
   X represents a halogen selected from the group consisting of fluorine (F), chlorine (Cl), bromine (Br) and Iodine (I) or X represents an anhydride group —O—(C=O)—R'3, wherein R'3 independently has the meaning as defined for R3;
   wherein in the formula (IV):
   R4 is a $C_1$-$C_4$-perfluoroalkyl or a $C_1$-$C_4$ chlorofluoroalkyl, and
   Y represents a halogen at any position in R4, and wherein the halogen is selected from chlorine (Cl), bromine (Br) and Iodine (I).

2. The process of claim 1, wherein the compound comprises one or more aromatic rings and wherein an aromatic ring of the starting material compound is reacted with a Friedel-Crafts reagent in the presence of an activated antimony pentahalide catalyst ($SbHal_5$) and activated by hydrogen fluoride (HF), and wherein the compound prepared is a fluorinated compound.

3. The process of claim 1, wherein the halogen in Rn is fluorine (F) or chlorine (Cl).

4. The process of claim 1, wherein the substituted $C_1$-$C_4$ alkoxy in Rn is a difluoralkoxy or trifluoralkoxy group.

5. The process of claim 1, wherein the substituted $C_1$-$C_4$ alkoxy in Rn is a difluormethoxy or trifluormethoxy group.

6. The process of claim 1, wherein the halogen in R'n is fluorine (F) or chlorine (Cl).

7. The process of claim 1, wherein the substituted $C_1$-$C_4$alkoxy in R'n is a difluoralkoxy or trifluoralkoxy group.

8. The process of claim 1, wherein the substituted $C_1$-$C_4$ alkoxy in R'n is a difluormethoxy or trifluormethoxy group.

9. The process of claim 1, wherein R1 and R2 independently from each other denote a hydrogen, a tri-halogeno methyl group (—$CHal_3$), a halogenocarbonyl group ((—C=O)Hal) or a halogeno methyl group (—$CH_2$Hal), and at least one of R1 and R2 is a tri-halogeno methyl group (—CHalh), a halogeno carbonyl group ((—C=O)Hal) or a halogeno methyl group (—$CH_2$Hal), and wherein each halogen (Hal) is chlorine (Cl).

10. The process of claim 1, wherein R3 is a $C_1$-$C_4$-perfluoroalkyl or a $C_1$-$C_4$ chlorofluoroalkyl.

11. The process of claim 1, wherein Y is chlorine (Cl).

* * * * *